US012758939B2

(12) United States Patent
Tu et al.

(10) Patent No.: US 12,758,939 B2
(45) Date of Patent: Oct. 13, 2026

(54) CO2 METHANATION USING PLASMA CATALYSIS

(71) Applicant: THE UNIVERSITY OF LIVERPOOL, Liverpool (GB)

(72) Inventors: Xin Tu, Liverpool (GB); Ni Wang, Liverpool (GB)

(73) Assignee: THE UNIVERSITY OF LIVERPOOL, Liverpool (GB)

( * ) Notice: Subject to any disclaimer, the term of this patent is extended or adjusted under 35 U.S.C. 154(b) by 49 days.

(21) Appl. No.: 18/001,783

(22) PCT Filed: Jun. 15, 2021

(86) PCT No.: PCT/GB2021/051479
§ 371 (c)(1),
(2) Date: Dec. 14, 2022

(87) PCT Pub. No.: WO2021/255421
PCT Pub. Date: Dec. 23, 2021

(65) Prior Publication Data

US 2023/0234018 A1 Jul. 27, 2023

(30) Foreign Application Priority Data

Jun. 15, 2020 (GB) ...................................... 2009093

(51) Int. Cl.
*B01J 35/45* (2024.01)
*B01J 19/08* (2006.01)
(Continued)

(52) U.S. Cl.
CPC ............. *B01J 19/088* (2013.01); *B01J 23/34* (2013.01); *B01J 23/755* (2013.01); *B01J 35/33* (2024.01);
(Continued)

(58) Field of Classification Search
CPC ........ B01J 19/088; B01J 23/34; B01J 23/755; B01J 35/33; B01J 35/40; B01J 35/45;
(Continued)

(56) References Cited

U.S. PATENT DOCUMENTS 11,591,226 B1 * 2/2023 Sunkara .................... C01B 3/04
2008/0135807 A1 * 6/2008 Adams .................... C01B 3/503 123/3

(Continued)

FOREIGN PATENT DOCUMENTS

EP 3050865 A1 8/2016
KR 20120134420 A 12/2012
WO WO-2014158095 A1 * 10/2014 .............. B01J 35/45

OTHER PUBLICATIONS

Lin et al. "Effect of Ni particle size on the production of renewable methane from CO2 over Ni/CeO2 catalyst", Journal of Energy Chemistry 61, (2021) 602-611. (Year: 2021).*

(Continued)

*Primary Examiner* — Tam M Nguyen
(74) *Attorney, Agent, or Firm* — Hoffman Warnick LLC

(57) ABSTRACT

An apparatus for forming methane from carbon dioxide and hydrogen is described. The apparatus comprises: a dielectric barrier discharge, DBD, device arranged to generate a plasma; and a passageway having an inlet for the carbon dioxide and the hydrogen and an outlet for the methane and including therein a catalyst comprising nickel and alumina. The passageway extends, at least in part, through the DBD device wherein, in use, the carbon dioxide is exposed to the catalyst in the presence of the hydrogen in the generated plasma, thereby forming the methane from at least some of the carbon dioxide and the hydrogen. A method, a use and a catalyst are also described.

4 Claims, 22 Drawing Sheets

(51) Int. Cl.

| | |
|---|---|
| ***B01J 23/34*** | (2006.01) |
| ***B01J 23/755*** | (2006.01) |
| ***B01J 35/33*** | (2024.01) |
| ***B01J 35/40*** | (2024.01) |
| ***B01J 37/34*** | (2006.01) |
| ***C07C 1/12*** | (2006.01) |

(52) U.S. Cl.

CPC ............... *B01J 35/40* (2024.01); *B01J 35/45* (2024.01); *B01J 37/347* (2013.01); *C07C 1/12* (2013.01); *B01J 2219/0805* (2013.01); *B01J 2219/0871* (2013.01); *B01J 2235/00* (2024.01); *B01J 2235/15* (2024.01); *B01J 2235/30* (2024.01); *C07C 2523/34* (2013.01); *C07C 2523/755* (2013.01)

(58) Field of Classification Search

CPC .............. B01J 37/347; B01J 2219/0805; B01J 2219/0871; B01J 2235/00; B01J 2235/15; B01J 2235/30; B01J 35/615; B01J 35/633; B01J 2219/0809; B01J 2219/083; B01J 2219/0883; C07C 1/12; C07C 2523/34; C07C 2523/755

See application file for complete search history.

(56) References Cited

U.S. PATENT DOCUMENTS

| | | | | |
|---|---|---|---|---|
| 2016/0052837 | A1* | 2/2016 | Chen | B01J 35/392<br>502/259 |
| 2022/0040656 | A1* | 2/2022 | Bromberg | B01J 19/0006 |
| 2022/0340499 | A1* | 10/2022 | Chang | B01J 19/088 |
| 2023/0234019 | A1* | 7/2023 | Tu | B01J 19/088<br>568/840 |
| 2025/0320126 | A1* | 10/2025 | Baroi | B01D 53/8671 |

OTHER PUBLICATIONS

PCT International Search Report and Written Opinion for International Application No. PCT/GB2021/051479, dated Sep. 24, 2021, 9 pages.

Great Britain Search Report for Application No. GB2009093.2, dated Nov. 25, 2020, 2 pages.

Jwa et al., "Nonthermal plasma-assisted catalytic methanation of CO and CO2 over nickel-loaded alumina," WIT Transactions on Ecology and the Environment, Energy and Sustainability III, vol. 143, 2011, pp. 361-368.

Biset-Peiro et al., "On the role of ceria in Ni—Al2O3 catalyst for CO2 plasma methanation," Applied Catalysis A: General, vol. 575, pp. 223-229.

Zeng et al., "Plasma-catalytic hydrogenation of CO2 for the cogeneration of CO and CH4 in a dielectric barrier discharge reactor: effect of argon addition," J. Phys. D: Appl. Phys., vol. 50, 31 pages.

Liying Lan et al., "CO2 hydrogenation to lower hydrocarbons over ZSM-5-supported catalysts in a dielectric-barrier discharge plasma reactor," Catalysis Communications, Elsevier, vol. 130, 2019, 6 pages.

Zhao et al., "Ni/Al2O3 catalysts for syngas methanation: Effect of Mn promoter," Journal of Natural Gas Chemistry, ScienceDirect, vol. 21, 2012, pp. 170-177.

Xu et al., "Mechanistic study of non-thermal plasma assisted CO2 hydrogenation over Ru supported on MgAl layered double hydroxide," Applied Catalysis B: Environmental 268 (2020).

Wang et al., "Shielding Protection by Mesoporous Catalysts for Improving Plasma-Catalytic Ambient Ammonia Synthesis," Journal of the American Chemical Society 144: 12020-12031 (2022).

Mehta et al., "Overcoming ammonia synthesis scaling relations with plasma-enabled catalysis," Nature Catalysis 1: 269-275 (2018).

Applicant, Further Experimental Data demonstrating differences between the behavior of catalysts observed in plasma and thermal systems, 6 pages, prepared May 7, 2026.

* cited by examiner

CO2 METHANATION USING PLASMA CATALYSIS

FIELD

The present invention relates to catalysts, for example catalysts for use in methanation processes. Particularly, the present invention relates to such catalysts comprising nickel for use in methanation using a non-thermal plasma generated by dielectric barrier discharge (DBD).

BACKGROUND TO THE INVENTION

Global warming, which is linked to carbon emissions, is a significant challenge. The average atmospheric temperature is rising, which acts as a driver for the collapse of biodiversity and the deprivation of sustainable territories. The atmospheric level of carbon dioxide has unprecedentedly topped 415 parts per million, according to sensors at the Mauna *Loa* Observatory in Hawaii.

Carbon dioxide reduction is a critical factor in alleviating climate change. Besides pressing for emission cuts, many studies are devoted to commodity chemical synthesis via carbon dioxide conversion. More specifically, carbon dioxide could be hydrogenated to value-added chemicals such as carbon monoxide, methane, methanol, ethanol, olefins and other hydrocarbons (for example, isoparaffins, aromatics) which are easier forms of energy storage and for use in industrial machining as a renewable substitute for fossil fuels.

Among various products of carbon dioxide conversion, methane can be converted into a liquid fuel and/or used for in the production of ammonia, carbon black and urea; it is also an essential ingredient in the production of methanol, acetylene, ethylene, formaldehyde, chloroform and tetrachloride.

However, the most difficult barrier in carbon dioxide utilization is to overcome the thermodynamically inert character of carbon dioxide. Numerous research works have been conducted to develop "methane favourable" catalysts to enhance carbon dioxide conversion rates and methane selectivity in carbon dioxide methanation. For example, nickel and ruthenium have been demonstrated as the most effective metals in the thermochemical hydrogenation of carbon dioxide into methane.

According to extensive studies on carbon dioxide methanation, conventional thermochemical routes incur counterproductive energy expenditure because of the high temperatures (200-500° C.) for a reasonable conversion. One promising avenue is therefore the exploration of novel catalysts, and the other one is to find a substitutable technology. Recently, catalysis-assisted non-thermal plasma technology, which opens the prospect of energy-efficient carbon dioxide conversion, has been widely used to circumvent the inherent barriers of the thermal catalytic process. The energetic electrons can activate molecules via excitation, dissociation and ionization. The reactive species (i.e. radicals, ions, excited species) generated in the plasma contribute to both the gas phase reactions and surface reactions, initiating new reaction pathways at low temperatures and ambient pressure.

However, some plasma-catalytic carbon dioxide methanation processes still use additional heating or adiabatic apparatus. The competitive advantage of the plasma is negated by the external convection heater (temperature ranging from 125° C. to 350° C.), for example.

Thus, there is a need to improve plasma-catalytic carbon dioxide methanation.

SUMMARY OF THE INVENTION

It is one aim of the present invention, amongst others, to provide an apparatus and method for converting carbon dioxide and hydrogen into methane, which at least partially obviates or mitigates at least some of the disadvantages of the prior art, whether identified herein or elsewhere. For instance, it is an aim of embodiments of the invention to provide an apparatus to provide plasma-catalytic synthesis of methane from carbon dioxide and hydrogen, with a high carbon dioxide conversion, methane selectivity, methane yield and/or energy efficiency. For instance, it is an aim of embodiments of the invention to provide a method of synthesising methane from carbon dioxide and hydrogen at low temperature using plasma. For instance, it is an aim of embodiments of the invention to provide an apparatus for and/or a method of carbon dioxide methanation that does not require additional heating and can be conducted at ambient pressure. For instance, it is an aim of embodiments of the invention to provide an apparatus for and/or a method of carbon dioxide methanation that may be integrated with renewable energy sources (e.g. wind and solar power), especially the use of intermittent renewable energy during peak load for localised or distributed energy storage.

DETAILED DESCRIPTION OF THE INVENTION

According to the present invention there is provided an apparatus, as set forth in the appended claims. Also provided is a method and a use. Other features of the invention will be apparent from the dependent claims, and the description that follows.

Apparatus

According to a first aspect, there is provided an apparatus for forming methane from carbon dioxide and hydrogen, the apparatus comprising:

- a dielectric barrier discharge, DBD, device arranged to generate a plasma; and
- a passageway having an inlet for the carbon dioxide and the hydrogen and an outlet for the methane and including therein a catalyst comprising nickel on a support comprising alumina;
- wherein the passageway extends, at least in part, through the DBD device wherein, in use, the carbon dioxide is exposed to the catalyst in the presence of the hydrogen in the generated plasma, thereby forming the methane from at least some of the carbon dioxide and the hydrogen.

The apparatus is suitable for forming methane from carbon dioxide and hydrogen. The apparatus is for forming methane gas from carbon dioxide and hydrogen. For the avoidance of doubt, the carbon dioxide and hydrogen are provided in gaseous form. Other products may be formed, for example water, carbon monoxide and/or other short chain hydrocarbons such as ethane.

However, these gaseous products will suitably be present in low amounts and methane gas will be the major product formed, for example 99.5% or more. In one example, the apparatus comprises a separation unit for separating the methane gas.

The apparatus comprises the DBD device.

Generally, DBDs are self-sustaining electrical discharges between electrodes having an insulating material (i.e. the dielectric barrier) in the discharge path (also known as a discharge zone). The dielectric is responsible for self-pulsing of the plasma, resulting in a nonthermal plasma at ambient pressures. Typically, dielectrics include glass, quartz, ceramics, enamel, mica, polymeric compositions and silicon rubber. Other dielectrics are known. The discharge gap is typically 1 to 10 mm, so as to allow operation at ambient pressures and moderate voltage amplitudes. Alternating current or pulsed high-voltage, typically in a range from about 1 kV to 100 kV at frequencies in a range from about 50 Hz to 1 MHz, are required due to the capacitive properties of the electrode and dielectric assembly. Planar configurations of DBDs include volume DBDs, surface DBDs and coplanar DBDs. Other configurations include sliding discharge, capillary plasma electrode discharge, microplasma array, plasma jets and axial electrode arrangements, such as used for DBD reactors.

In one example, the DBD device comprises a set of electrodes, including a first electrode and a second electrode, having a dielectric barrier there between. In one example, the set of electrodes is arranged in a coaxial configuration. In one example, the DBD device comprises a coaxial DBD. In this way, an annular discharge zone may be formed. In one example, the first electrode comprises and/or is a first tube, for example a cylindrical tube (i.e. an outer electrode), and the second electrode comprises and/or is a wire, a rod or a second tube, for example a cylindrical wire (i.e. an inner electrode), coaxial therewithin, wherein the dielectric barrier is in contact with the first electrode or the second electrode. In other words, the first electrode may be an outer tube and the second electrode may be an inner wire. For example, the dielectric barrier may be provided on internal surfaces of the first electrode, in which the plasma is formed in the gas at the surface of the dielectric barrier and propagates radially across a volume to the second electrode. Additionally and/or alternatively, the dielectric barrier may be provided on outer surfaces of the second electrode, in which the plasma is formed in the gas at the surface of the dielectric barrier and propagates readily across a volume to the first electrode.

It should be understood that the electrodes are thus electrical conductors. In one example, the first electrode comprises and/or is a metallic electrode, for example a metal or alloy. In one example, the first electrode comprises and/or is a metallic plate, sheet, film or wire electrode. For example, electrodes may be provided by solid metal plate or sheet, by printing metal films on the dielectric, by etching of circuit boards, by depositing metallic film or paste on the dielectric or by using wire mesh, for example. Other electrodes are known. The second electrode may be as described with respect to the first electrode. In one example, the dielectric barrier has a dielectric constant k (i.e. relative permittivity) at 20° C. in a range from 2 to 500, preferably in the range from 3 to 250. In one example, the dielectric barrier comprises and/or is glass, quartz, ceramic, enamel, mica, a polymeric composition and/or silicon rubber. Suitable glasses include silicate glass, such as soda lime glass, borosilicate glass, lead glass, aluminosilicate glass, and silica—free glass.

In one example, the DBD device comprises: a quartz tube (i.e. providing the passageway) having a gas inlet (i.e. the inlet) in an upper portion thereof and the outlet in a lower portion thereof; an inner electrode (i.e. a second electrode) having, for example, a cylindrical rod shape and provided in the quartz glass tube; an outer electrode (i.e. a first electrode), for example stainless steel mesh, around at least in part the outer surface of the quartz glass tube; and the catalyst contained in the quartz tube between the inner electrode and the outer electrode (i.e. a coaxial configuration).

In one example, the inner electrode comprises and/or is a stainless steel rod or wire and the outer electrode comprises and/or is a cylindrical tubular stainless-steel mesh coaxial therewith.

In one example, the apparatus comprises a gas supply unit for supplying the carbon dioxide ($CO_2$) gas and/or the hydrogen ($H_2$) gas.

In one example, the gas supply unit further supplies nitrogen ($N_2$) or argon (Ar) gas to generate, at least in part, the DBD plasma. However, this may not be preferred. In one preferred example, no further gas is supplied to generate the DBD plasma.

The passageway includes therein the catalyst comprising nickel on an alumina support.

In one example, the catalyst is provided in the form of particles, granules, pellets, tablets plates and/or conglomerates thereof. In one example, the catalyst is provided in the form of particles, for example, granules, having an average particle diameter $D_{50}$ in a range from 0.05 mm to 1.0 mm, preferably in a range from 0.1 mm to 0.75 mm, more preferably in a range from 0.25 mm to 0.50 mm or 0.45 mm, for example 40-60 mesh (about 0.25 mm to 0.42 mm). The particle size distribution may be controlled by sieving, for example. Other methods of measuring the average particle diameter will be known by the skilled person. In one example, the average particle diameter $D_{50}$ is relatively larger, for example in a range from 0.05 mm to 10 mm, preferably in a range from 0.1 mm to 7.5 mm, more preferably in a range from 0.25 mm to 5 mm In one example, the alumina comprises and/or is $\gamma$-$Al_2O_3$. $\gamma$-$Al_2O_3$ is preferred to $\alpha$-$Al_2O_3$, for example, having a higher Brunauer-Emmett-Teller (BET) surface area. Activated $Al_2O_3$ may also be used.

It should be understood that the catalyst is affixed to the support. For example, the catalyst may be impregnated in the support (i.e. prepared by impregnation). Additionally and/or alternatively, the supporter catalyst may be prepared by co-precipitation.

In one example, the alumina has a BET specific surface area in a range from 200 to 300 $m^2/g$, and has a pore volume in a range from 0.4 to 0.8 $cm^3/g$ with a pore size in a range from 3.5 nm to 4.0 nm. In one example, these physical properties could be measured using a standard $N_2$-physisorption measurements, for example as known by the skilled person. For example, $N_2$ adsorption-desorption may be conducted using a Micrometeritics ASAP 2020 Sorptometer at −196° C. Prior to measurement, the samples are degassed at 300° C. for 6 h. The specific surface areas may be estimated via the BET method in the $P/P_0$ values ranging from 0.05 to 0.3 of the fresh catalysts.

In one example, the alumina comprises pores having a pore size in a range from 3.5 nm to 4.0 nm, suitably in a range from 3.6 nm to 3.9 nm, suitably in a range from 3.7 nm to 3.85 nm, for example in a range from 3.75 to 3.82 nm. In one example, the pore size is measured using an $N_2$-adsorption process. This process will be known by the skilled person. Other suitable methods of measuring the pore size are known.

In one example, the support comprises $SiO_2$, $BaTiO_3$, $TiO_2$, $CeO_2$, $ZrO_2$, MgO, CaO and/or a zeolite.

The inventors have established that a catalyst comprising nickel is particularly suitable for plasma-catalytic $CO_2$ methanation reactions. In one example, the apparatus of the first aspect, when in use, obtains a high $CO_2$ conversion, $CH_4$ selectivity, yield and/or energy efficiency without using any heating equipment.

In one example, the catalyst comprises nickel in a range from 1 to 35 wt. %, preferably in a range from 2 to 30 wt. %, more preferably in a range from 3 to 25 wt. %, even more preferably in a range from 5 to 20 w.t % nickel, most preferably in a range from 7 to 15 wt. % nickel, by weight of the support.

In one example, the catalyst consists essentially (at least 99 wt. % by weight of the catalyst) or consists (at least 99.9 wt. % by weight of the catalyst) of nickel and optionally species thereof and unavoidable impurities. Unavoidable impurities include, for example, other metals.

In one preferred example, the catalyst comprises and/or is an alumina support impregnated with metallic nickel.

In one example, the catalyst is prepared using incipient wetness impregnation OW or IWI), which is also known in the art as capillary impregnation or dry impregnation. In one example, a nickel precursor is dissolved in an aqueous or organic solution and the nickel-containing solution is added to a porous alumina support. Capillary action draws the solution into the pores. The catalyst may then be dried and optionally calcined to drive off the volatile components within the solution, thereby depositing nickel on the alumina surface. Methods of preparing such catalysts are well known. In one example, calcining is performed at a temperature in a range from 400 to 600° C., for a time in a range from 4 hours to 6 hours and/or at a heating rate in a range from 5° C. per minute to 10° C. per minute.

In one example, the catalyst comprises an alumina support impregnated with nickel. In one example, the alumina support is impregnated with metal precursors of nitrate hydrate for nickel (II) before the calcination.

In one example, the nickel precursor is nickel nitrate.

In one example, the catalyst comprises metallic nickel. In one example, the catalyst comprises a metallic nickel species after thermal reduction of NiO/alumina in $H_2$, $H_2$/Ar and/or $N_2/H_2$. In one example, the nickel is dispersed to the alumina support.

In one example, the catalyst comprises nickel particles. In one example, the nickel particles have a mean particle diameter $D_{50}$ in a range from 1 nm to 10 nm, preferably in a range from 2 nm to 8 nm, more preferably in a range from 3 nm to 5 nm. Generally, smaller particles are preferred. Methods of measuring the mean particle diameter are known, for example, using transmission electron microscopy (TEM) or high-resolution transmission electron microscopy (HRTEM).

In one example, the nickel particles are evenly distributed, for example dispersed, on the alumina support. In one example, the nickel particles are uniformly distributed on the alumina support. In one example, the nickel particles are regularly distributed on the alumina support. In one example, the nickel particles are homogenously distributed on the alumina support. The distribution of the nickel particles may be determined, for example qualitatively and/or quantitatively, using TEM, HRTEM and/or CO adsorption, for example.

In one example, the catalyst comprises one or more rare earth elements for example cerium, one or more first row and/or second row transition metals for example manganese and/or zirconium and/or one or more alkaline metals for example magnesium, and/or mixtures thereof. These rare earth elements, first row and/or second row transition metals and/or alkaline metals may be present as promoters. In one preferred example, the catalyst comprises manganese.

Without being bound by any theory, it is understood that the addition of such promoters affects the distribution of nickel species-on the alumina support when in use. Manganese, for example, may weaken an interaction between the nickel species and the support and/or may affect the aggregation of Ni particles.

In one example, the catalyst comprises one or more promoters, as described above, in a range from 0.01 to 10 wt. %, preferably in a range from 0.1 to 7 wt. %, more preferably in a range from 0.5 to 5 wt. %, most preferably in a range from 0.7 to 3 wt. %, by weight of the alumina.

In one preferred example, the catalyst comprises manganese in a range from 0.01 to 10 wt. %, preferably in a range from 0.1 to 7 wt. %, more preferably in a range from 0.5 to 5 wt. %, most preferably in a range from 0.7 to 3 wt. %, by weight of the alumina.

In one especially preferred example, the catalyst consists essentially (at least 99 wt. % by weight of the catalyst) or consists (at least 99.9 wt. % by weight of the catalyst) of alumina, nickel and manganese and unavoidable impurities.

Any promoters (for example, manganese) may be added during preparation using suitable precursors (for example, manganese nitrate).

In one example, the apparatus comprises a source of external heat to provide additional heat to the reaction when in use. However, this is not preferred. In one preferred example, the apparatus does not comprise an or any external heating source(s).

The apparatus may comprise additional safety features. For example, the apparatus may comprise a cooling source to reduce temperature when the apparatus is in use. However, this is not preferred. In one example, the apparatus is used at low temperature and thus no additional cooling sources are needed.

This offers a significant advantage over conventional apparatuses, which often operate at high temperatures and are therefore energy-intensive. Additionally and/or alternatively, conventional apparatuses typically require cooling, since the methanation reaction is exothermic, to attenuate heating. In contrast, the apparatus according to the first aspect may not require additional cooling since the reaction temperature is relatively low.

Method

According to a second aspect, there is provided a method of forming methane from carbon dioxide and hydrogen, the method comprising:

- generating a plasma using a dielectric barrier discharge, DBD, device; and
- exposing the carbon dioxide to a catalyst comprising nickel on a support comprising alumina in the presence of hydrogen in the generated plasma, thereby forming the methane from at least some of the carbon dioxide and hydrogen.

In one example, the method is carried out using an apparatus according to the first aspect.

The methane, the carbon dioxide, the hydrogen, the plasma, the DBD device, the catalyst, the nickel, the support and/or the alumina may be as described with respect to the first aspect. The method may include any of the steps and/or features described with respect to the first aspect, mutatis mutandis.

In one example, the reaction temperature (i.e. the temperature at which the carbon dioxide is exposed to the catalyst in the presence of hydrogen in the generated plasma) is in a range from 35 to 180° C., preferably in a range from 50 to 150° C., more preferably in a range from 75 to 135° C., most preferably in a range from 85 to 120° C.

In one example, the method comprises externally heating the carbon dioxide, the catalyst and/or the hydrogen, for example using an external source of heat. In one preferred example, the method comprises no external heating. In this way, the reaction heat is provided, for example at least partly and/or fully, by the generated plasma, and/or partly and/or fully by the heat of reaction.

The method according to the second aspect offers a significant advantage over conventional methods as the reaction may be performed at relatively low temperatures, without an external source of heat. This reduces the energy consumption of the process. Additionally and/or alternatively, since the reaction may be performed at relatively low temperatures, the method may be initiated (i.e. switched on) and/or paused or terminated (i.e. switched off) on demand, for example immediately or instantly, since preheating is not required, for example.

Since the generated plasma reaches a stable state in a relatively short time, the method may be stopped and subsequently restarted without any additional waiting time, improving an efficiency of the process. In this way, the process provides great flexibility to be integrated with renewable energy sources such as wind and solar power, especially the use of intermittent renewable energy during peak load for localised or distributed energy storage.

In one example, the method comprises activating the catalyst using, at least in part, the generated plasma, for example by supplying an electrical power in a range of 0.72 to 20 kJ/L, preferably in a range of from 1 to 6 kJ/L, relative to the gas flow rate (L/min). This may also be defined as the specific energy input (SEI).

The conversion $X_{CO_2}$ of carbon dioxide may be defined by Equation (1):

$$X_{CO_2}(\%) = \frac{CO_2\ \text{converted (mol/s)}}{CO_2\ \text{input (mol/s)}} \times 100 \tag{1}$$

In one example, the method has a conversion $X_{CO_2}$, as defined by equation (1), of carbon dioxide to methane of at least 70%, preferably at least 85%, more preferably at least 90%.

The conversion $X_{H_2}$ of hydrogen may be defined by Equation (2):

$$X_{H_2}(\%) = \frac{H_2\ \text{converted (mol/s)}}{H_2\ \text{input (mol/s)}} \times 100 \tag{2}$$

Suitably the method has a conversion $X_{H_2}$, as defined by equation (2), of hydrogen to methane of at least 72%, preferably at least 80%, more preferably at least 88%.

The selectivity $S_{CH_4}$ of methane may be defined by Equation (3):

$$S_{CH_4}(\%) = \frac{CH_4\ \text{produced (mol/s)}}{CO_2\ \text{converted (mol/s)}} \times 100 \tag{3}$$

In one example, the method has a selectivity $S_{CH_4}$ of methane of at least 85%, preferably at least 90%, more preferably at least 95%, most preferably at least 99%. In one especially preferred example, the method has a selectivity $S_{CH_4}$ of methane of at least 99.5%.

The carbon monoxide and alkyl product selectivities $S_{CO}$, $S_{C_mH_n}$ respectively may be defined by Equations (4) and (5) respectively:

$$S_{CO}(\%) = \frac{CO\ \text{produced (mol/s)}}{CO_2\ \text{converted (mol/s)}} \times 100 \tag{4}$$

$$S_{C_mH_n}(\%) = \frac{m \times C_mH_n\ \text{produced (mol/s)}}{CO_2\ \text{converted (mol/s)}} \times 100 \tag{5}$$

where:

$C_mH_n$, is the gas product which includes $C_2H_2$, $C_2H_4$, $C_2H_6$, $C_3H_6$, $C_3H_8$, $C_4H_8$ and $C_4H_{10}$.

The yield $Y_{CH_4}$ of methane is calculated using Equation (6):

$$Y_{CH_4}(\%) = \frac{CH_4\ \text{produced (mol/s)}}{CO_2\ \text{input (mol/s)}} \times 100 \tag{6}$$

In one example, the method has a yield $Y_{CH_4}$ of methane at least 30%, preferably at least 45%, more preferably at least 60%, most preferably at least 75%. In one especially preferred example, the method has a yield $Y_{CH_4}$ of methane at least 76%.

The space time yield of methane $STY_{CH_4}$ may be defined by Equation (7):

$$STY_{CH_4}(\text{mol/g/s}) = \frac{CH_4\ \text{produced (mol/s)}}{m_{cat}(g) \times w(\%)} \tag{7}$$

where:

$m_{cat}$ is the total weight of catalyst (g); and w is the weight fraction of metal in the calcined sample (wt. %).

In one example, the method has a yield $STY_{CH_4}$ of methane of at least 203 μmol/$g_{metal}$/s, preferably at least 1400 μmol/$g_{metal}$/s.

The energy efficiencies $E_{CO_2}$, $E_{CH_4}$, of plasma $CO_2$ methanation, defined as the moles of $CO_2$ converted and $CH_4$ produced per kilowatt-hour, may be calculated using Equations (8) and (9), respectively:

$$E_{CO_2}(\text{mol/kWh}) = \frac{CO_2\ \text{converted (mol/h)}}{\text{Discharge power (kW)}} \tag{8}$$

$$E_{CH_4}(\text{mol/kWh}) = \frac{CH_4\ \text{produced (mol/h)}}{\text{Discharge power (kW)}} \tag{9}$$

In one example, the method has an energy efficiency $E_{CO_2}$, $E_{CH_4}$, of at least 0.4 mol/kWh, preferably at least 4 mol/kWh, more preferably at least 8 mol/kWh, most preferably at least 17 mol/kWh. In one especially preferred example, the method has an energy efficiency of at least 18 mol/kWh.

In one example, exposing the carbon dioxide to the catalyst in the presence of hydrogen in the generated plasma comprises exposing the carbon dioxide to the catalyst in the presence of hydrogen in the generated plasma at approximately ambient pressure. It should be understood that approximately ambient pressure is the substantially natural pressure of the environment, for example about 101 kPa.

The method comprises exposing the carbon dioxide to the catalyst comprising nickel and alumina in the presence of hydrogen in the generated plasma, thereby forming the methane from at least some of the carbon dioxide and hydrogen.

In one example, the method comprises exposing the carbon dioxide to the catalyst comprising nickel and alumina in the presence of other gases, for example inert gases such as argon and/or nitrogen and/or reactive gases such as oxygen, amongst others. However, one preferred example only carbon dioxide and hydrogen and unavoidable impurities are present, notwithstanding reaction products including methane.

In one example, exposing the carbon dioxide to the catalyst in the presence of hydrogen in the generated plasma comprises exposing the carbon dioxide to the catalyst in the presence of an excess of hydrogen (i.e. relative to a stoichiometric $H_2/CO_2$ ratio of 2:1). For example, in one preferred embodiment carbon dioxide and hydrogen are provided in a $H_2/CO_2$ ratio of 2:1-5:1.

Use

According to a third aspect, there is provided use of a catalyst comprising nickel on a support comprising alumina for plasma-activated catalysis of methanation.

The catalyst, the nickel, the support, the alumina, the DBD device, the methane, the carbon dioxide, and/or the hydrogen and/or the plasma, may be as described with respect to the first aspect and/or the second aspect. The use may include any of the steps and/or features described with respect to the first aspect and/or the second aspect, mutatis mutandis.

According to a fourth aspect, there is provided a catalyst comprising nickel on a support comprising alumina.

The catalyst, the nickel, the support and/or the alumina may be as described with respect to the first aspect.

Definitions

Throughout this specification, the term "comprising" or "comprises" means including the component(s) specified but not to the exclusion of the presence of other components. The term "consisting essentially of" or "consists essentially of" means including the components specified but excluding other components except for materials present as impurities, unavoidable materials present as a result of processes used to provide the components, and components added for a purpose other than achieving the technical effect of the invention, such as colourants, and the like.

The term "consisting of" or "consists of" means including the components specified but excluding other components.

Whenever appropriate, depending upon the context, the use of the term "comprises" or "comprising" may also be taken to include the meaning "consists essentially of" or "consisting essentially of", and also may also be taken to include the meaning "consists of" or "consisting of".

The optional features set out herein may be used either individually or in combination with each other where appropriate and particularly in the combinations as set out in the accompanying claims. The optional features for each aspect or exemplary embodiment of the invention, as set out herein are also applicable to all other aspects or exemplary embodiments of the invention, where appropriate. In other words, the skilled person reading this specification should consider the optional features for each aspect or exemplary embodiment of the invention as interchangeable and combinable between different aspects and exemplary embodiments.

BRIEF DESCRIPTION OF THE DRAWINGS

For a better understanding of the invention, and to show how exemplary embodiments of the same may be brought into effect, reference will be made, by way of example only, to the accompanying diagrammatic Figures, in which:

FIGS. 6A to 6F show metal particle size dispersion of fresh catalysts after reduction on: FIG. 6A $Fe/Al_2O_3$; FIG. 6B $FeMn/Al_2O_3$; FIG. 6C $Cu/Al_2O_3$; FIG. 6D $CuMn/Al_2O_3$; FIG. 6E $Ni/Al_2O_3$; FIG. 6F $NiMn/Al_2O_3$;

FIG. 11A NiZrAl; FIG. 11B NiMgAl; FIG. 11C NiCeAl; and FIG. 11D NiMnAl;

DETAILED DESCRIPTION OF THE DRAWINGS

Experimental

Figure 1A:
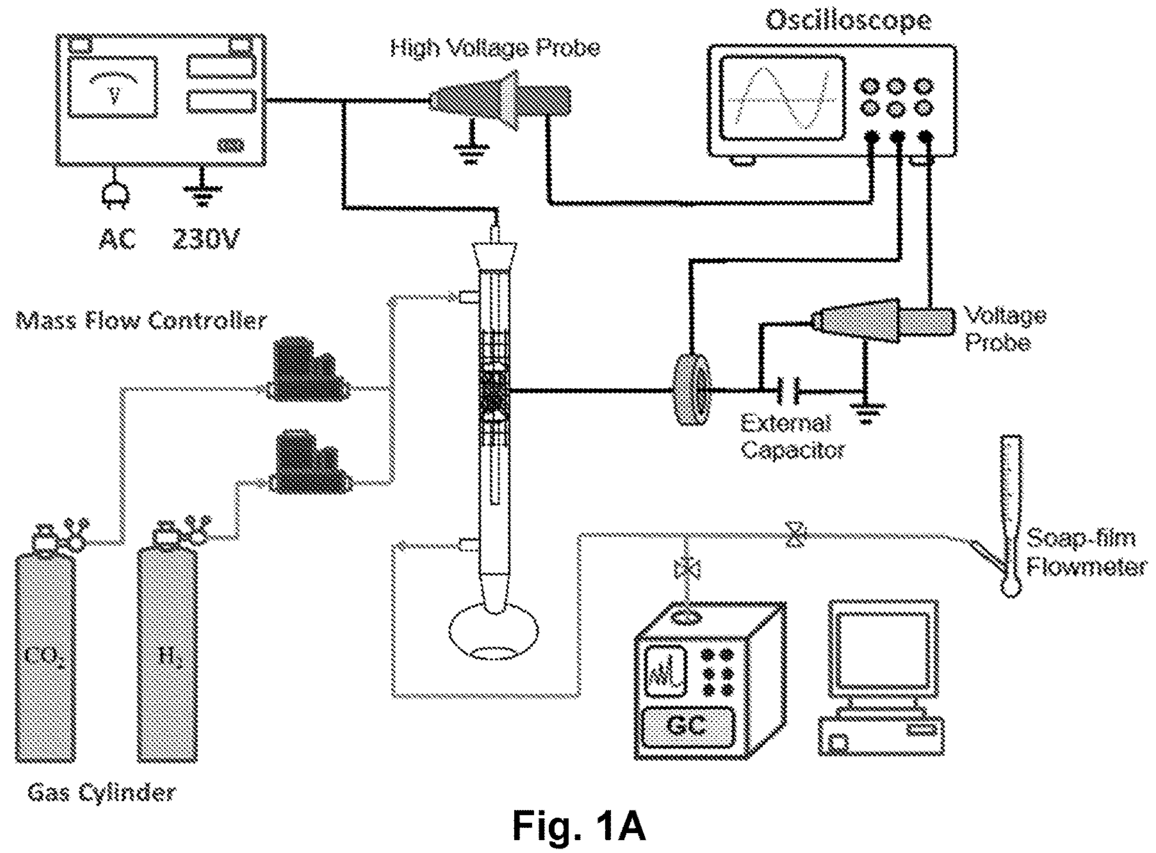
FIG. 1A schematically depicts the experimental setup.

The following procedures were used in the examples which follow.

$N_2$ adsorption-desorption was conducted using a Micromeritics ASAP 2020 Sorptometer at −196° C. Prior to measurement, the samples were degassed at 300° C. for 6 h. The specific surface areas were estimated via the Brunauer-Emmett-Teller (BET) method in the $P/P_0$ values ranging from 0.05 to 0.3 of the fresh catalysts.

Transmission electron microscopy (TEM) analysis was performed with a FEI Tecnai G2 f20 s-twin microscope (200 kV). The average particle size was determined by the Nano Measurer software through more than 5 micrographs and around 200 particles for each catalyst. Moreover, an X-ray energy dispersive spectrometer (EDS) was utilized in conjunction with a STEM HAADF detector for elemental mapping.

Powder X-ray diffraction (XRD) patterns were recorded in a Bruker AXS Advance $D_8$ diffractometer (40 kV, 40 mA) using Cu $K_\alpha$ radiation as the X-ray source. For each sample Bragg angle was set between 5° and 80° (2θ) with a scan speed of 0.05°/s. The JCPDS standard cards were used for the identification of different phases.

X-ray photoelectron spectroscopy (XPS) was used to study both chemical composition and oxidation state of the catalyst surfaces. Photoelectron spectra were recorded with a Thermo Scientific ESCALAB 250Xi spectrometer equipped with Al—$K_\alpha$ radiation (hv=1486.6 eV). The corresponding binding energies were calibrated with the C 1s line at 284.8 eV as a reference.

The $H_2$ temperature-programmed reduction ($H_2$-TPR) was performed in a Micromeritics AutoChem 2920 instrument. About 50 mg fresh sample was firstly pretreated under pure Ar at 300° C. for 1 h to remove the impurities on the catalyst surface, and then cooled down to 30° C. After that, the reduction of the catalysts was carried out over a 10% $H_2$/Argon flow in 30 mL/min with the temperature raised to 900° C. (10° C./min).

The consumed hydrogen was monitored by a thermal conductivity detector (TCD). The ability of $CO_2$ adsorption and the acid site density on each catalyst was evaluated by $CO_2$ temperature programmed desorption ($CO_2$-TPD) in the same equipment. Previously to $CO_2$ adsorption, around 50 mg of the samples were reduced at 650° C. with 10 vol. % $H_2$/Ar for 60 min firstly, then purified with Ar for 40 min, and cooled to 50° C. After exposed to $CO_2$ for 1 h, the sample was flushed in Ar flow. The TPD profile was recorded in Ar from 50 to 900° C. (10° C./min).

EXAMPLES: PLASMA-CATALYTIC $CO_2$ HYDROGENATION TO METHANE

Example 1: $Ni/Al_2O_3$ Catalysts with Different Ni Loadings (1-20 wt. % $Ni/Al_2O_3$, Denoted as xNiAl, x=1, 4, 7, 10, 15, 20)

Figure 1B:
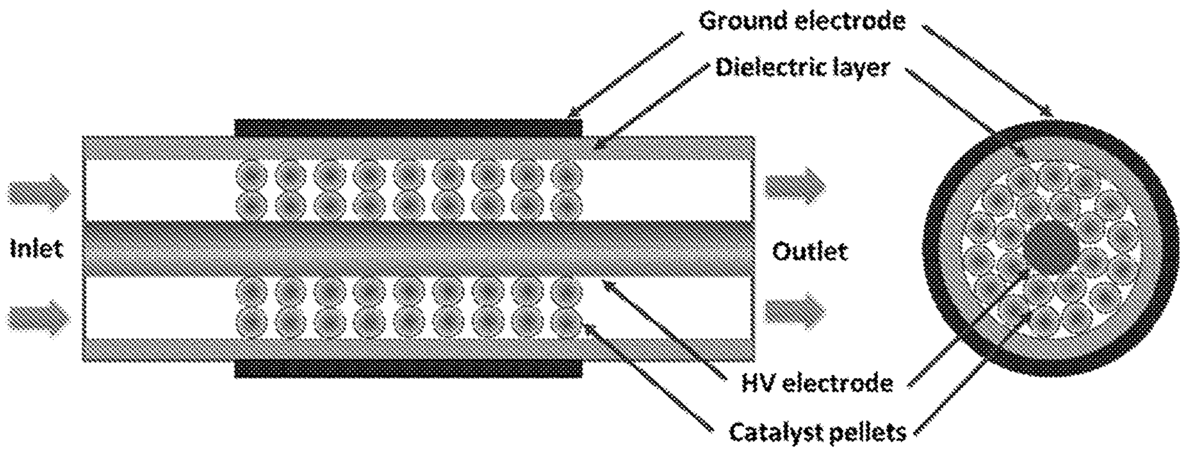
FIG. 1B schematically depicts an axial cross-section and a transverse cross-section of a DBD reactor.

FIG. 1A schematically depicts the experimental setup; and FIG. 1B schematically depicts an axial cross-section and a transverse cross-section of a DBD reactor.

Coaxial DBD plasma reactor without external heating or cooling (electrode gap: 2 mm; discharge length 6 cm; inner electrode (high voltage electrode): stainless steel (SS) rod, 2 mm diameter; outer electrode (ground electrode): SS mesh); specific energy input (SEI): 17 kJ/L; discharge power: 8.5 W.

Gas: $H_2/CO_2$=4:1 (total 30 ml/min); GHSV (gas hourly space velocity) 1792 $h^{-1}$.

Catalyst: 0.5 g; 40-60 mesh; packing length 4 cm; reaction temperature: 125-155° C.

TABLE 1

Physical properties of the fresh catalysts (after reduction)

| Catalysts | Surface area ($m^2$/g) [a] | Pore volume ($cm^3$/g) [a] |
|---|---|---|
| $Al_2O_3$ (comp) | 221 | 0.45 |
| 1NiAl | 209 | 0.41 |
| 4NiAl | 195 | 0.41 |
| 7NiAl | 174 | 0.36 |
| 10NiAl | 171 | 0.34 |
| 15NiAl | 166 | 0.33 |
| 20NiAl | 145 | 0.31 |

[a] Measured by $N_2$-adsorption

Figure 2A:
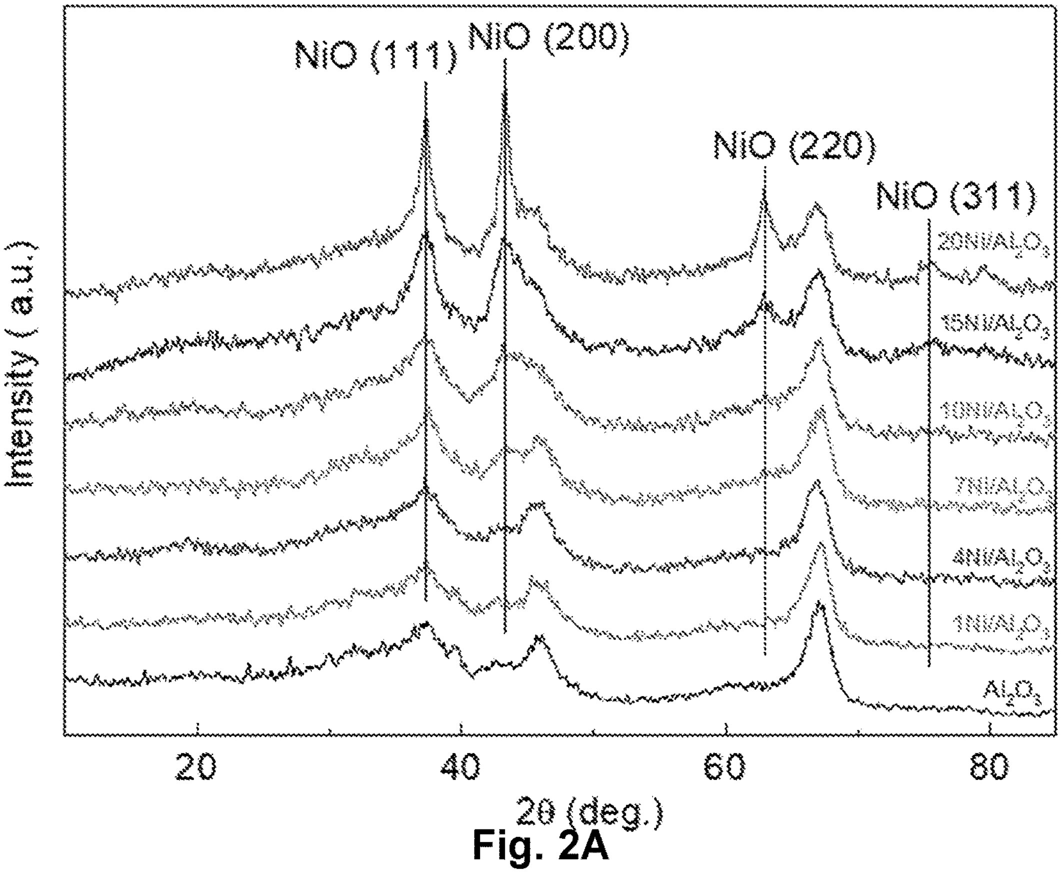
FIG. 2A shows XRD patterns of the fresh catalysts after calcination.
Figure 2B:
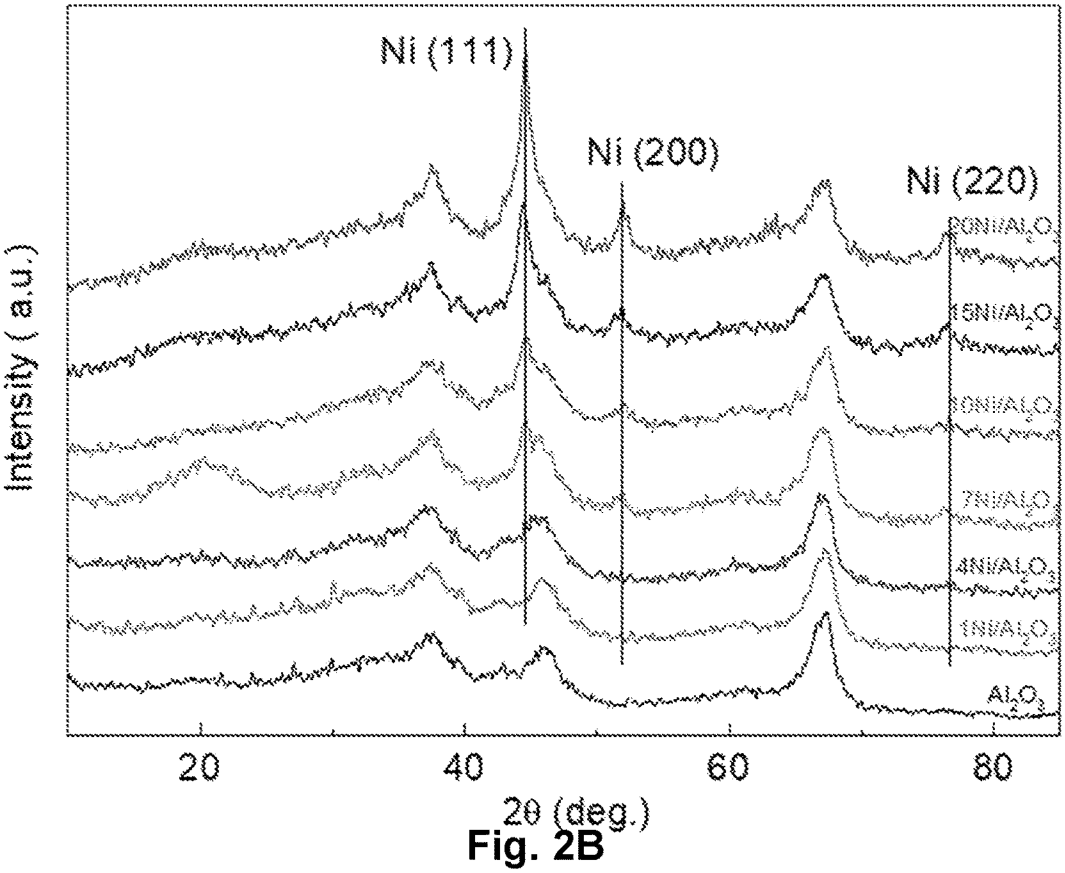
FIG. 2B shows XRD patterns of the fresh catalysts after reduction.

FIG. 2A shows XRD patterns of the fresh catalysts after calcination; and FIG. 2B shows XRD patterns of the fresh catalysts after reduction.

TABLE 2

Chemical properties of the fresh catalysts

| Catalysts | $H_2$ consumed (mmol/g) [a] | $CO_2$ desorbed (mmol/g) [b] |
|---|---|---|
| $Al_2O_3$ (comp) | — | 2.55 |
| 1NiAl | 0.11 | 2.40 |
| 4NiAl | 0.32 | 2.33 |
| 7NiAl | 0.43 | 2.24 |
| 10NiAl | 0.51 | 1.83 |
| 15NiAl | 1.51 | 1.74 |
| 20NiAl | 1.88 | 1.56 |

Figure 3A:
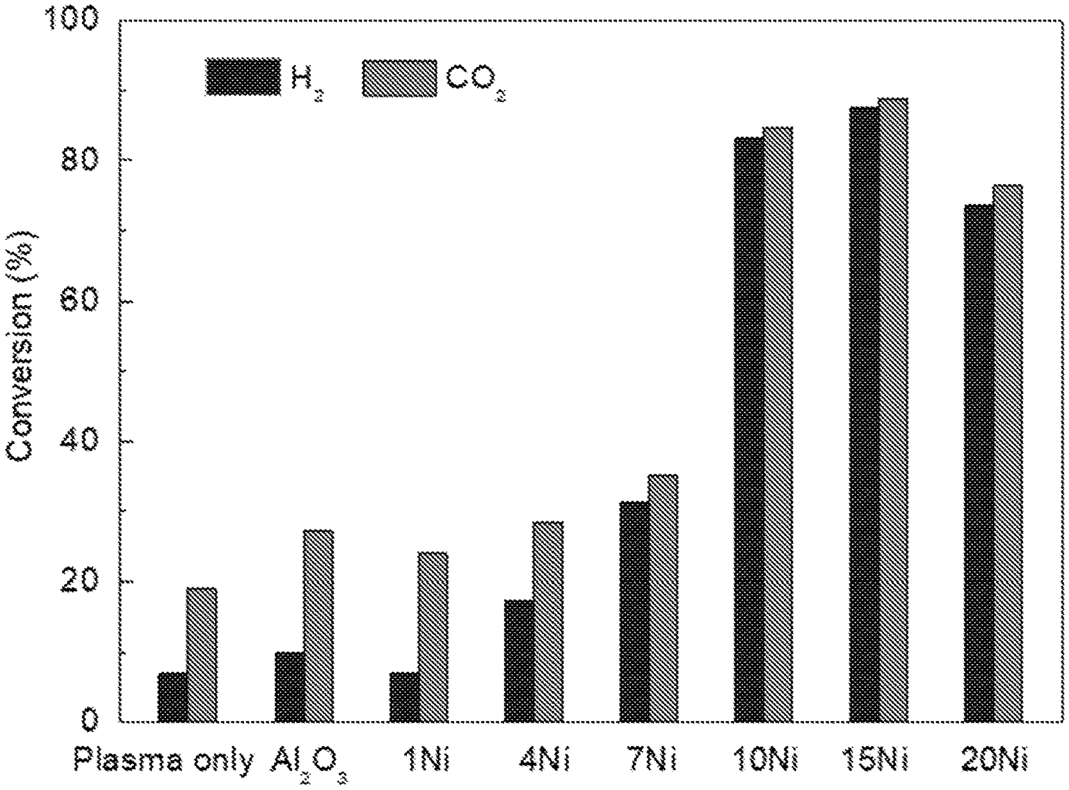
FIG. 3A shows conversion of $CO_2$ and $H_2$.
Figure 3B:
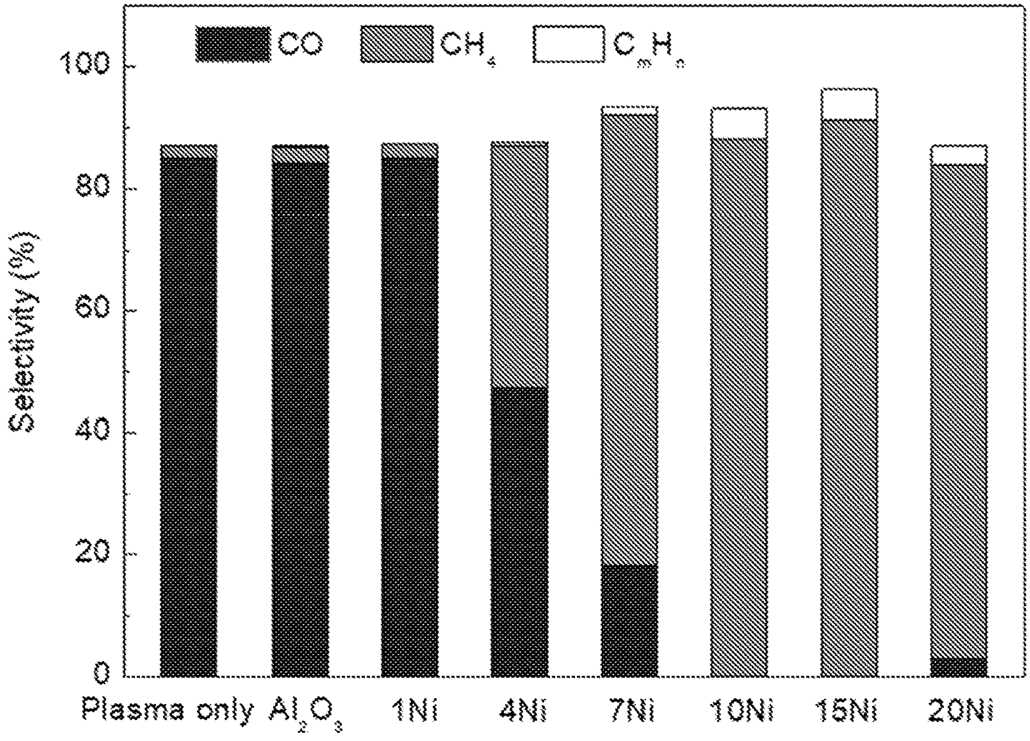
FIG. 3B shows gaseous product selectivities.
Figure 3C:
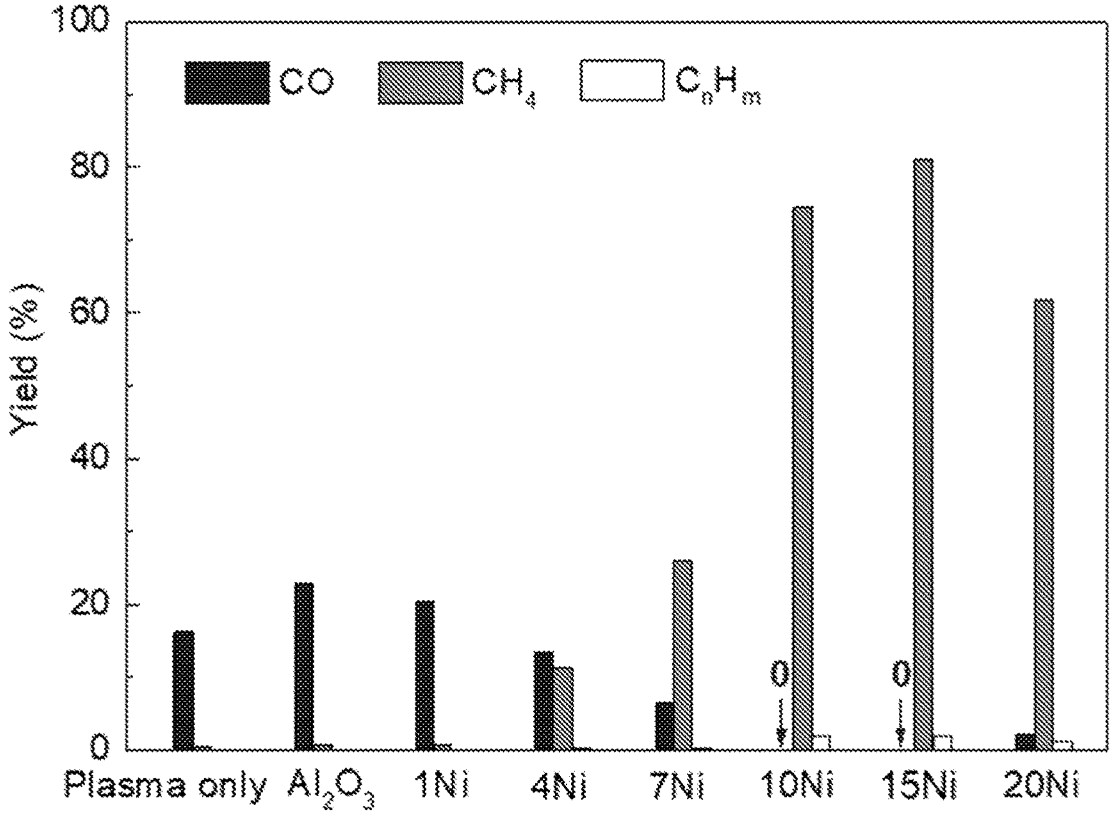
FIG. 3C shows gaseous product yields.
Figure 3D:
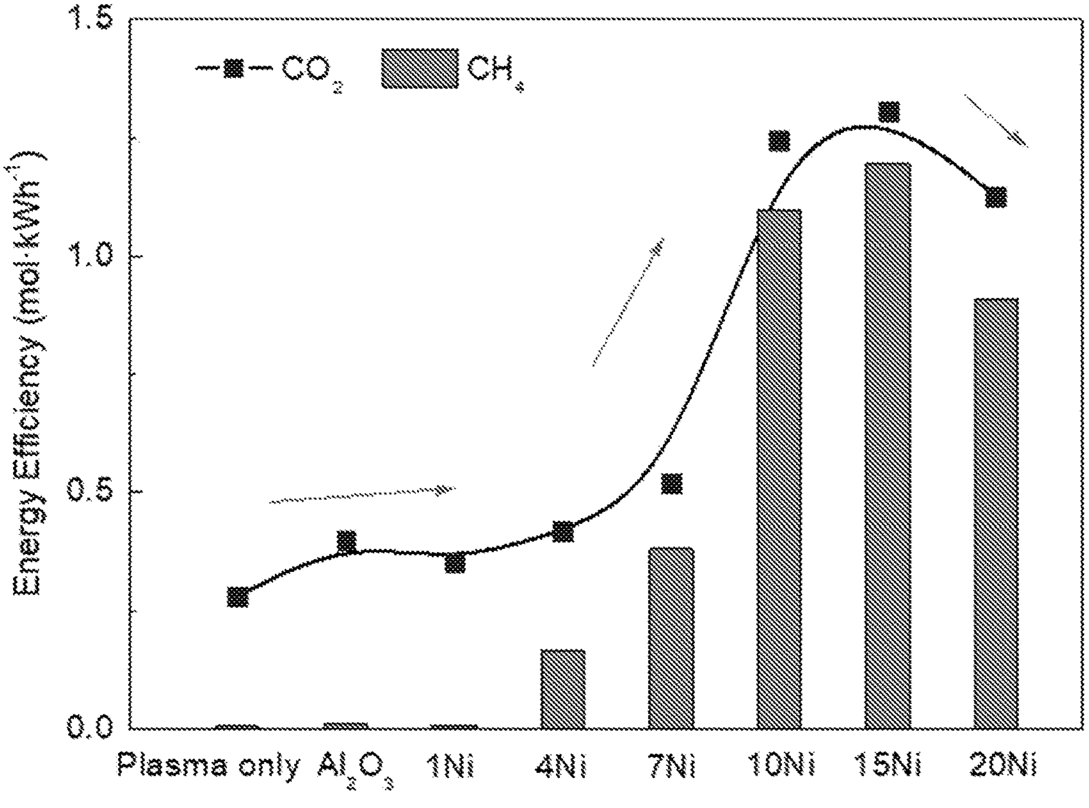
FIG. 3D shows energy efficiency for $CO_2$ conversion and $CH_4$ production ($H_2/CO_2$=4:1, GHSV=1792 $h^{-1}$, 1 atm, SEI=17 kJ/L)

[a] Calculated via $H_2$-TPR analysis of the fresh catalysts after calcination
[b] Calculated via $CO_2$-TPD analysis of the fresh catalysts after reduction FIG. 3A shows conversion of $CO_2$ and $H_2$; FIG. 3B shows gaseous product selectivities;

FIG. 3C shows gaseous product yields; and FIG. 3D shows energy efficiency for $CO_2$ conversion and $CH_4$ production ($H_2/CO_2$=4:1, GHSV=1792 $h^{-1}$, 1 atm, SEI=17 kJ/L).

Effect of Ni loading of $Ni/Al_2O_3$ catalysts (1 wt. %-20 wt. %): the 15NiAl catalyst (15 wt. % $Ni/Al_2O_3$) shows the highest conversion of $CO_2$ (90%) and selectivity of $CH_4$ (91%), providing the highest methane yield of ~81%.

Example 2: $X/Al_2O_3$ and $X/Mn/Al_2O_3$ (X═Fe, Cu and Ni) Catalysts

γ-$Al_2O_3$ supported metal (7 wt. %) catalysts were prepared by the incipient wetness impregnation method using iron nitrate ($Fe(NO_3)_3 \cdot 9H_2O$), cupric nitrate ($Cu(NO_3)_2 \cdot 2.5H_2O$) and nickel nitrate ($Ni(NO_3)_2 \cdot 6H_2O$) as the metal precursors respectively. Manganous nitrate ($Mn(NO_3)_2 \cdot 4H_2O$) also was added to the solution for 1 wt. % Mn containing catalysts. The impregnated samples and bare $Al_2O_3$ were dried in the air overnight before being put into the oven at 120° C. for 4 h, then calcined at 400° C. for 5 h in the muffle. After calcination, the samples were pre-reduced by the mixed gas of 30 mL/min $H_2$ and 170 mL/min Ar at 450° C. for 5 h. The obtained catalysts are denoted as X (X═Fe, Cu and Ni) and XMn.

Figure 4A:
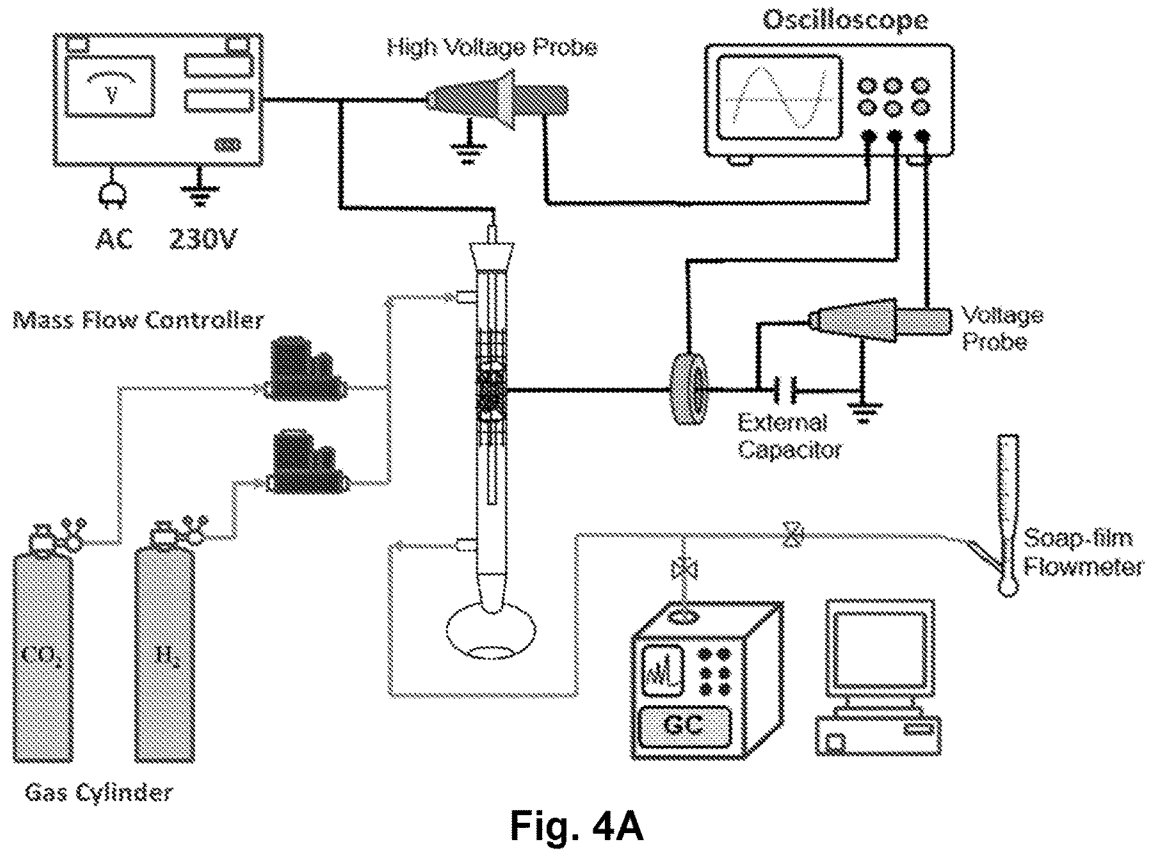
FIG. 4A schematically depicts the experimental setup.
Figure 4B:
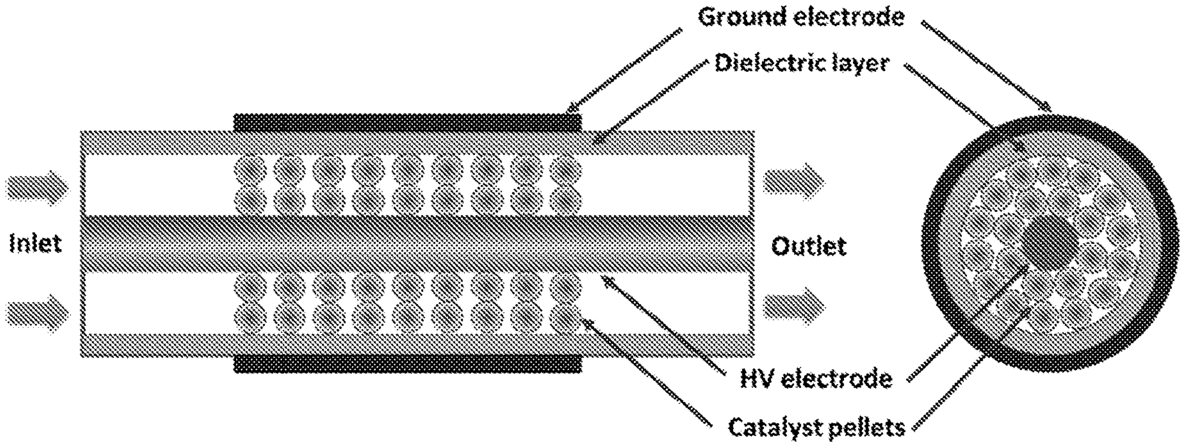
FIG. 4B schematically depicts an axial cross-section and a transverse cross-section of a DBD reactor.

FIG. 4A schematically depicts the experimental setup; and FIG. 4B schematically depicts an axial cross-section and a transverse cross-section of a DBD reactor.

As shown in FIG. 4B, a coaxial DBD reactor was employed in this study. An 8 cm long stainless-steel mesh was wrapped outside the quartz tube (14 mm external diameter and 10 mm inner diameter) and was grounded through an external capacitor $C_{ext}$ (0.47 ρF). A stainless-steel rod (diameter 5 mm) was fixed in the centre of the quartz tube as the high voltage electrode. The discharge gap was 2.5 mm. The DBD reactor was connected to a high voltage AC power supply (Suman). The total discharge power was fixed at 30 W under different experimental conditions. The specific energy input was fixed at 57 kJ/L. Soap-film flowmeter was used to measure the gas flow rate after the reaction. Catalyst (0.5 g) was packed in the center of the discharge area. The feed gas was composed of 20 ml/min $H_2$ and 10 ml/min $CO_2$ ($H_2/CO_2$=2:1).

Coaxial DBD plasma reactor without external heating or cooling (electrode gap: 2.5 mm; discharge length 8 cm; inner electrode: SS rod, 5 mm diameter; outer electrode SS mesh); SEI: 57 kJ/L; discharge power: 30 W.

Gas: $H_2/CO_2$=2:1 (total 30 ml/min); GHSV 2684 $h^{-1}$.

Catalyst: 0.5 g; 40-60 mesh; packing length 1.2 cm; reaction temperature: 85-120° C.

The gas products were analyzed by a gas chromatograph (Agilent GC 7820A) equipped with a flame ionization detector (FID) and a thermal conductivity detector (TCD). Each measurement was repeated three times and had a high reproducibility with a measurement error of less than 1%.

TABLE 3

Physical properties of the fresh catalysts (after reduction)

| Catalysts | Surface area ($m^2$/g) [a] | Pore volume ($cm^3$/g) [a] | Pore size (nm) [a] |
|---|---|---|---|
| $Al_2O_3$ (comp) | 221 | 0.45 | 3.8 |
| $Fe/Al_2O_3$ (comp) | 181 | 0.38 | 3.6 |
| $FeMn/Al_2O_3$ (comp) | 193 | 0.37 | 3.5 |
| $Cu/Al_2O_3$ (comp) | 194 | 0.40 | 3.9 |
| $CuMn/Al_2O_3$ (comp) | 201 | 0.38 | 3.9 |
| $Ni/Al_2O_3$ | 199 | 0.40 | 3.8 |
| $NiMn/Al_2O_3$ | 202 | 0.39 | 3.8 |

[a] Measured by $N_2$-adsorption

The Brunaur-Emmett-Teller (BET) specific surface area, pore volume and average pore diameter of the catalysts are listed in Table 3. The γ-$Al_2O_3$ support exhibits a surface area of 221 $m^2 \cdot g^{-1}$ which is larger than other catalysts. It is probably due to the part of dopant blocking of the pore structures. Also, by the addition of Mn promoter, the surface area is slightly larger than that of the catalysts without Mn.

Figure 5A:
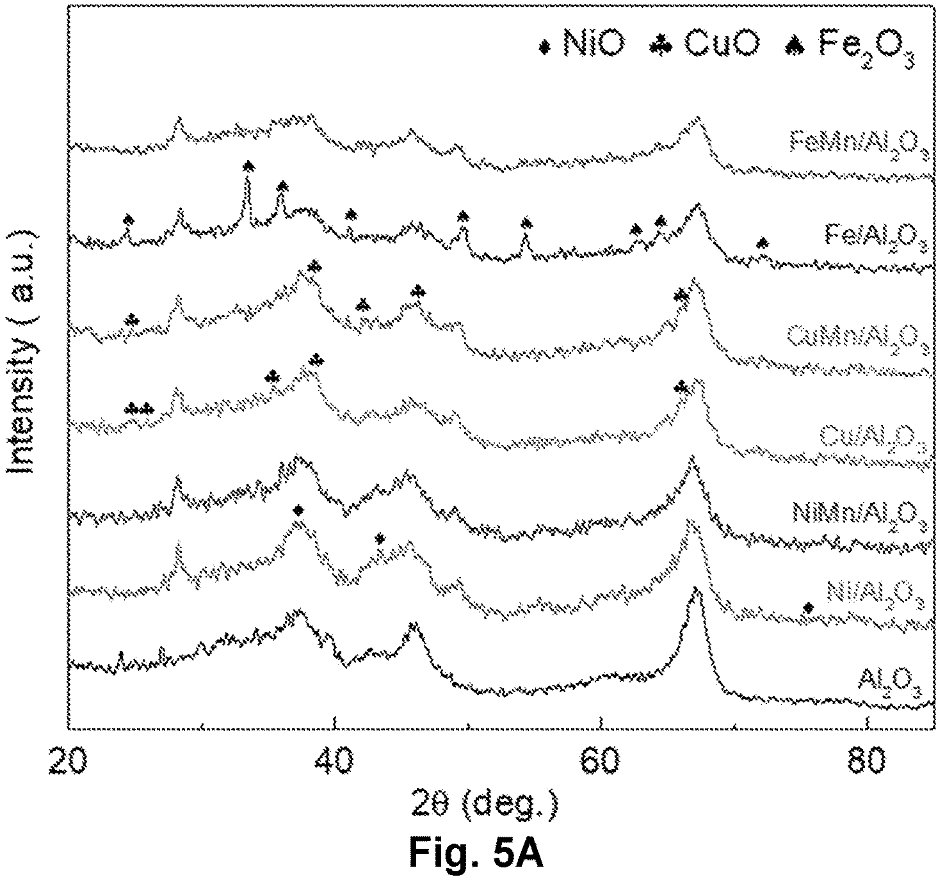
FIG. 5A shows XRD patterns of fresh catalysts after calcination.
Figure 5B:
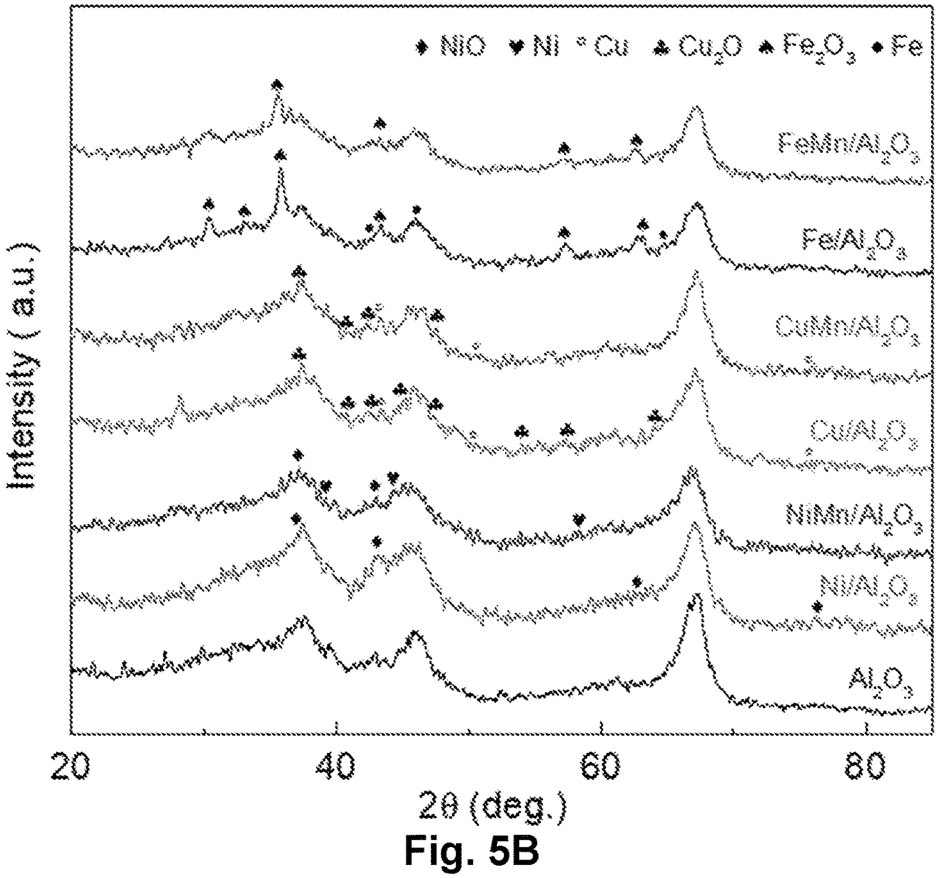
FIG. 5B shows XRD patterns of spent catalysts.

FIG. 5A shows XRD patterns of fresh catalysts after calcination; and FIG. 5B shows XRD patterns of spent catalysts.

The crystallite structures of the fresh and spent catalysts are presented in FIGS. 5A and 5B. The diffraction pattern for the $Al_2O_3$ has a number of peaks that can be well-indexed to γ-$Al_2O_3$ (JCPDS79-1558). Sharp and intense peaks appearing in the Fe can be indexed to $Fe_2O_3$ (JCPDS33-0664) and those in the Cu-based catalysts can be indexed to CuO (JCPDS44-0706). Meanwhile, NiO characteristic peaks in 37.2°, 43.3° and 62.9° (JCPDS47-1049), corresponding to the NiO (111), (200) and (220) crystal planes respectively, were detected on Ni. However, after Mn was added to the catalysts, no characteristic diffraction peaks of $MnO_x$ or metal-salt could be observed because of its lower loading content and weak crystallization. Furthermore, note that the diffraction peaks of the metallic oxides became weaker and broader, and even disappeared. These indicate that the particles on the supporter were smaller and evenly distributed.

According to the XRD patterns of the catalysts after the reaction, metallic Fe, Cu and Ni are detected, implying the different degrees of reduction for the metallic oxides during the reaction. This can be ascribed to the part of thermal $H_2$-reduction treatment before the plasma and interaction with the H species in the plasma.

Figure 6A:
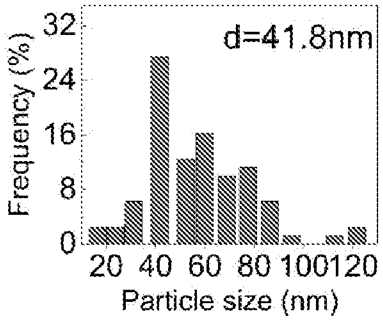
Figure 6B:
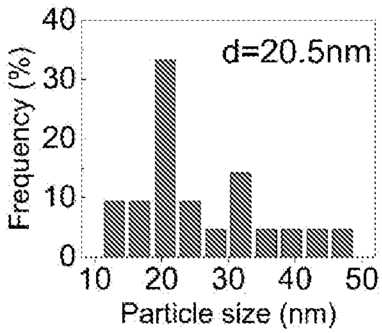
Figure 6C:
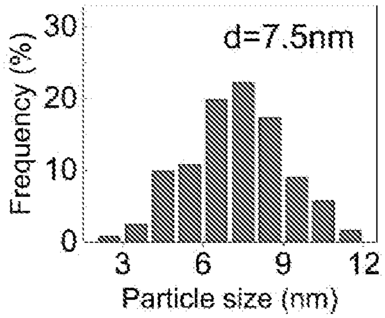
Figure 6D:
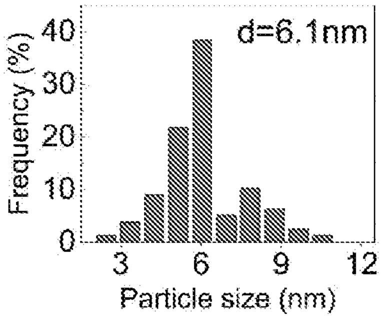
Figure 6E:
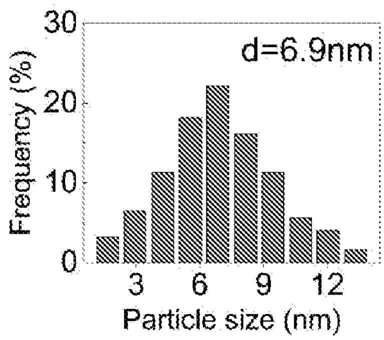
Figure 6F:
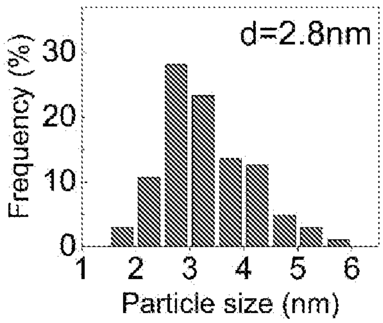

FIGS. 6A to 6F show metal particle size dispersion of fresh catalysts after reduction on: FIG. 6A $Fe/Al_2O_3$; FIG. 6B $FeMn/Al_2O_3$; FIG. 6C $Cu/Al_2O_3$; FIG. 6D $CuMn/Al_2O_3$; FIG. 6E $Ni/Al_2O_3$; FIG. 6F $NiMn/Al_2O_3$.

TABLE 4

Chemical properties of the catalysts

| Catalysts | $H_2$ consumed (mmol/g) [b] | $CO_2$ desorbed (mmol/g) [c] | Metal/Al (%) [d] |
|---|---|---|---|
| $Al_2O_3$ (comp) | — | 2.32 | — |
| $Fe/Al_2O_3$ (comp) | 0.40 | 2.23 | 3.32 |
| $FeMn/Al_2O_3$ (comp) | 0.54 | 1.48 | 3.04 |
| $Cu/Al_2O_3$ (comp) | 0.73 | 1.90 | 2.72 |
| $CuMn/Al_2O_3$ (comp) | 0.75 | 1.96 | 2.77 |
| $Ni/Al_2O_3$ | 0.62 | 1.67 | 2.76 |
| $NiMn/Al_2O_3$ | 0.76 | 1.98 | 3.69 |

a. Calculated via $H_2$-TPR analysis of the fresh catalysts after calcination
[b] Calculated via $CO_2$-TPD analysis of the fresh catalysts after reduction
[c] Calculated via XPS analysis of the fresh catalysts after reduction Effect of 7 wt. % $X/Al_2O_3$ and 7 wt. % X1 wt. % $Mn/Al_2O_3$ Catalysts (X═Fe, Cu and Ni)

Note the DBD reactor and operating conditions used in this experiment are different to those used in example 1 and 3, especially $H_2/CO_2$ molar ratio. The NiMn catalyst (7 wt. % Ni/1 wt. % $Mn/Al_2O_3$) shows the highest conversion of $CO_2$ and $CH_4$ selectivity. However, the performance of this catalyst under these conditions is lower than that shown in example 1 and 3. The NiMn catalyst is still very stable after running the reaction for 8 hours.

Figure 7A:
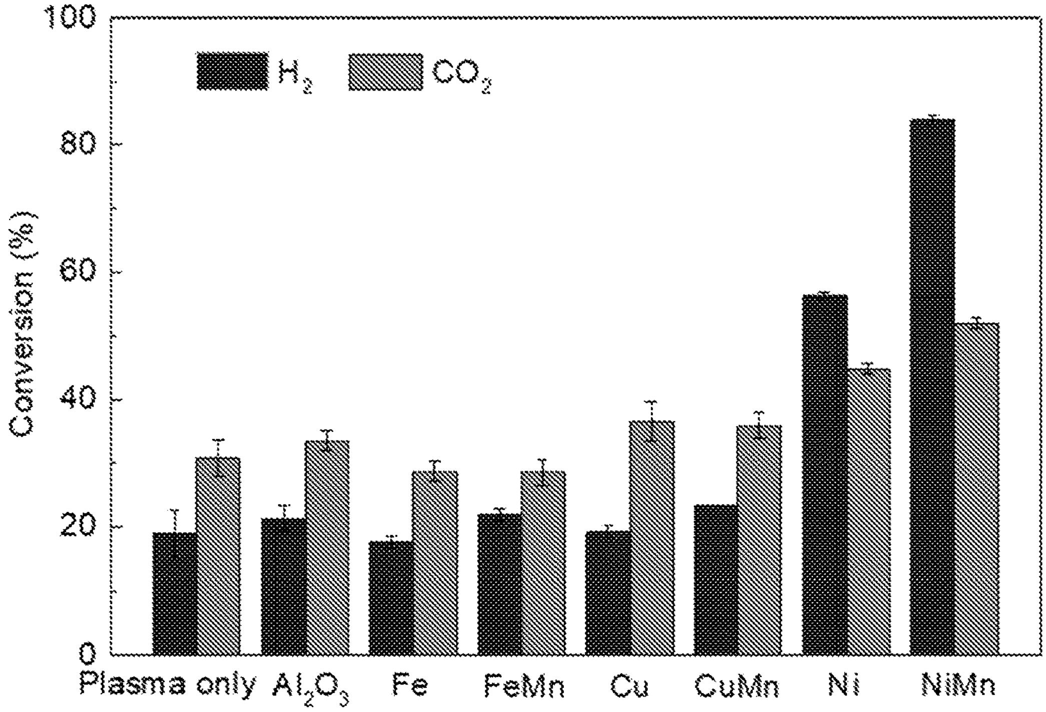
FIG. 7A shows $CO_2$ and $H_2$ conversions.
Figure 7B:
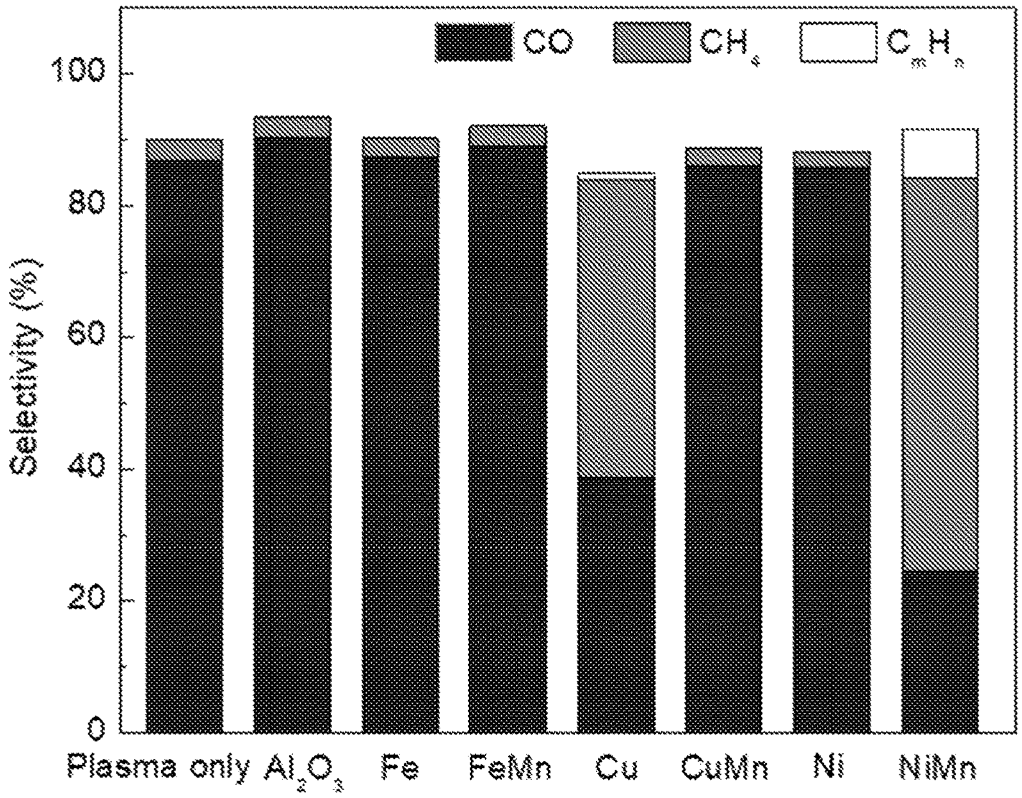
FIG. 7B gaseous product selectivities.
Figure 7C:
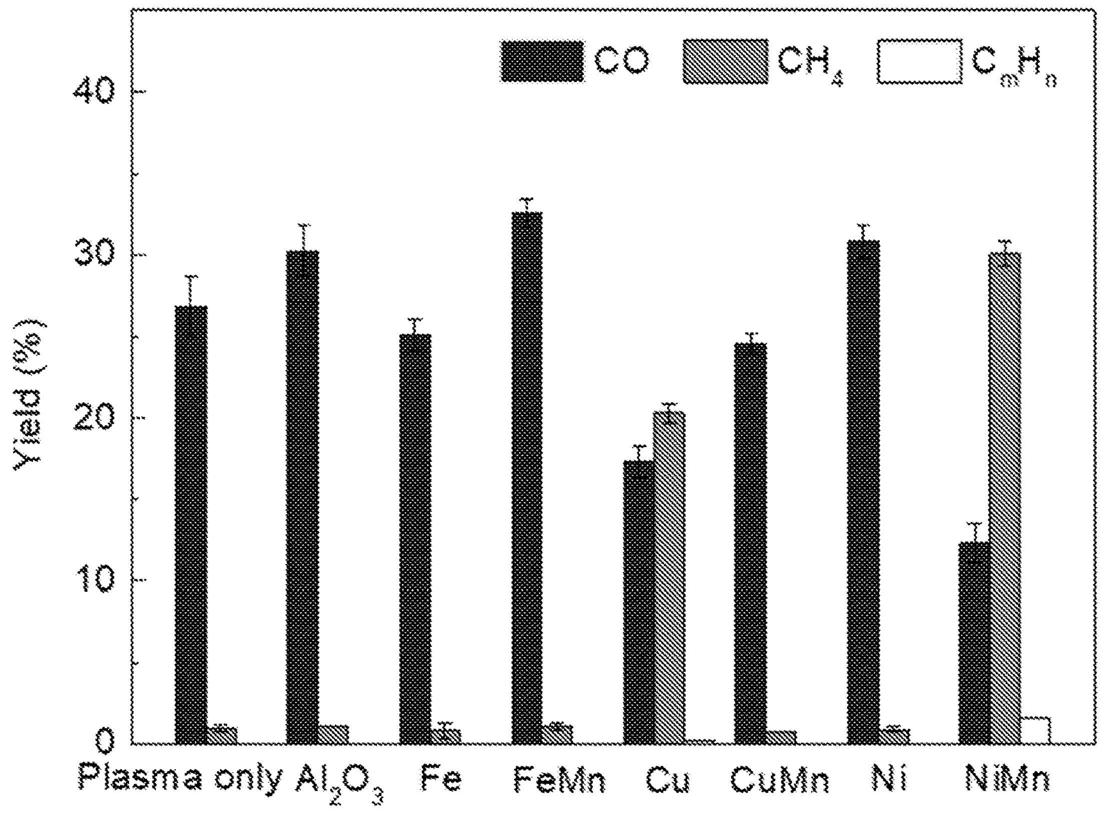
FIG. 7C shows gaseous product yields.
Figure 7D:
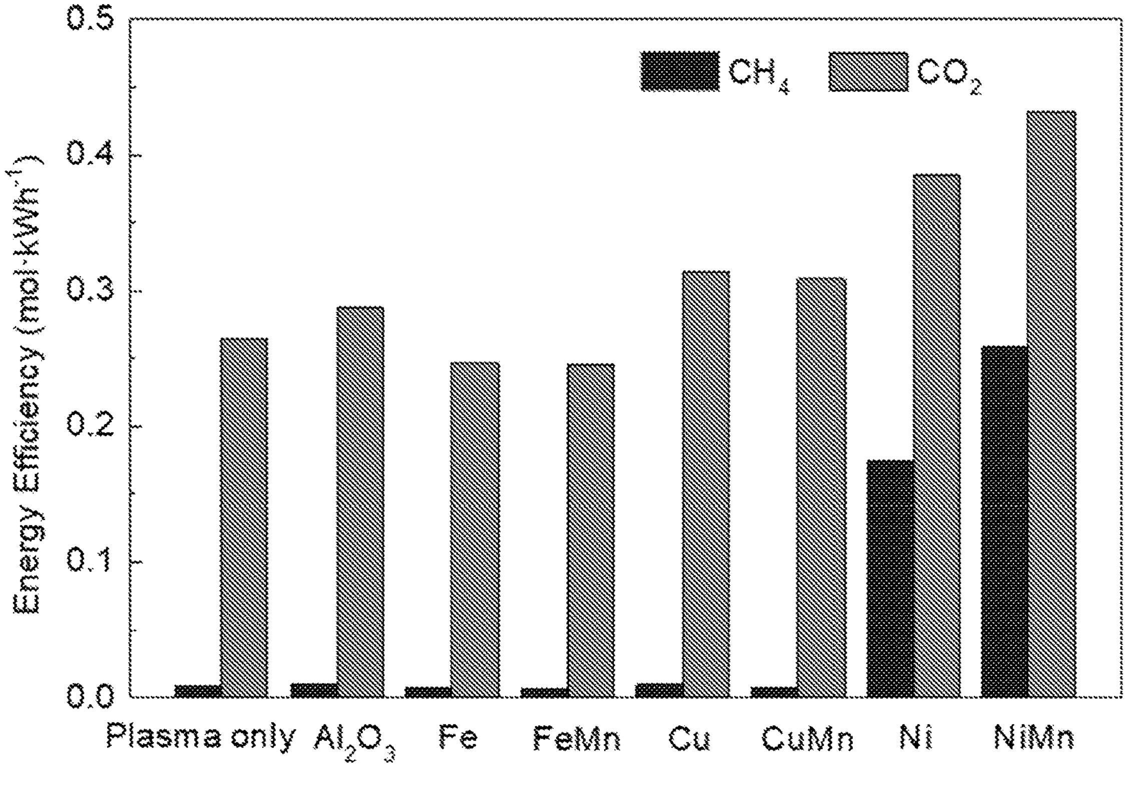
FIG. 7D shows $CO_2$ and $CH_4$ energy efficiencies ($H_2/CO_2$=2:1, GHSV=2684 $h^{-1}$, 1 atm, SEI=57 kJ/L)

FIG. 7A shows $CO_2$ and $H_2$ conversions; FIG. 7B gaseous product selectivities; FIG. 7C shows gaseous product yields; and FIG. 7D shows $CO_2$ and $CH_4$ energy efficiencies ($H_2/CO_2$=2:1, GHSV=2684 $h^{-1}$, 1 atm, SEI=57 kJ/L);

FIG. 7A shows $CO_2$ and $H_2$ conversion on $Al_2O_3$ and metal-loaded catalysts with the plasma. For the comparison, all of the catalysts were investigated in the same experimental conditions at low temperatures (85-120° C.) in a furnace and without plasma, which result in no conversion. With the presence of plasma, the $CO_2$ conversion for the catalysts without Mn follows the order Fe<plasma alone<$Al_2O_3$<Cu<Ni. After the addition of Mn, the $H_2$ conversions were slightly increased in Fe and Cu-based catalysts which are in good agreement with $H_2$-TPR results. However, there is no obvious promotion for $CO_2$ which indicates that the reactions still mainly occurred in the plasma gaseous phase. Interestingly, as to NiMn, $H_2$ and $CO_2$ conversions were considerably increased after Mn promotion, reaching nearly 50% for $CO_2$ and surpassing 80% for $H_2$ which are very closed to the limitation of the reaction equilibrium towards $CO_2$ methanation.

As presented in FIG. 7B, the product selectivities were also significantly affected combining with the catalysts, especially Ni-based catalysts. However, when it comes to Cu-based and Fe-based catalysts, their results are very similar with that using plasma only, most of the $CO_2$ conversion was triggered by $CO_2$ deoxygenation because of the electron collisions and decomposition to CO in the plasma. The $CH_4$ selectivity (around 45% for Ni) was further enhanced by the presence of Mn and reached a maximum of 60%. In this case, $CH_4$ becomes the main product whilst olefins, ethane, propane and butane as by-products. Other carbons in the liquid phase was dominated with methanol. Moreover, the $CH_4$ yield of NiMn was much higher than the sum of solo Mn and Ni catalysts. This might be a result of the stronger interaction and electron transfer between Ni and Mn metals rather than Fe or Cu, which contributed to the path of $CO_2$ methanation.

Figure 8:
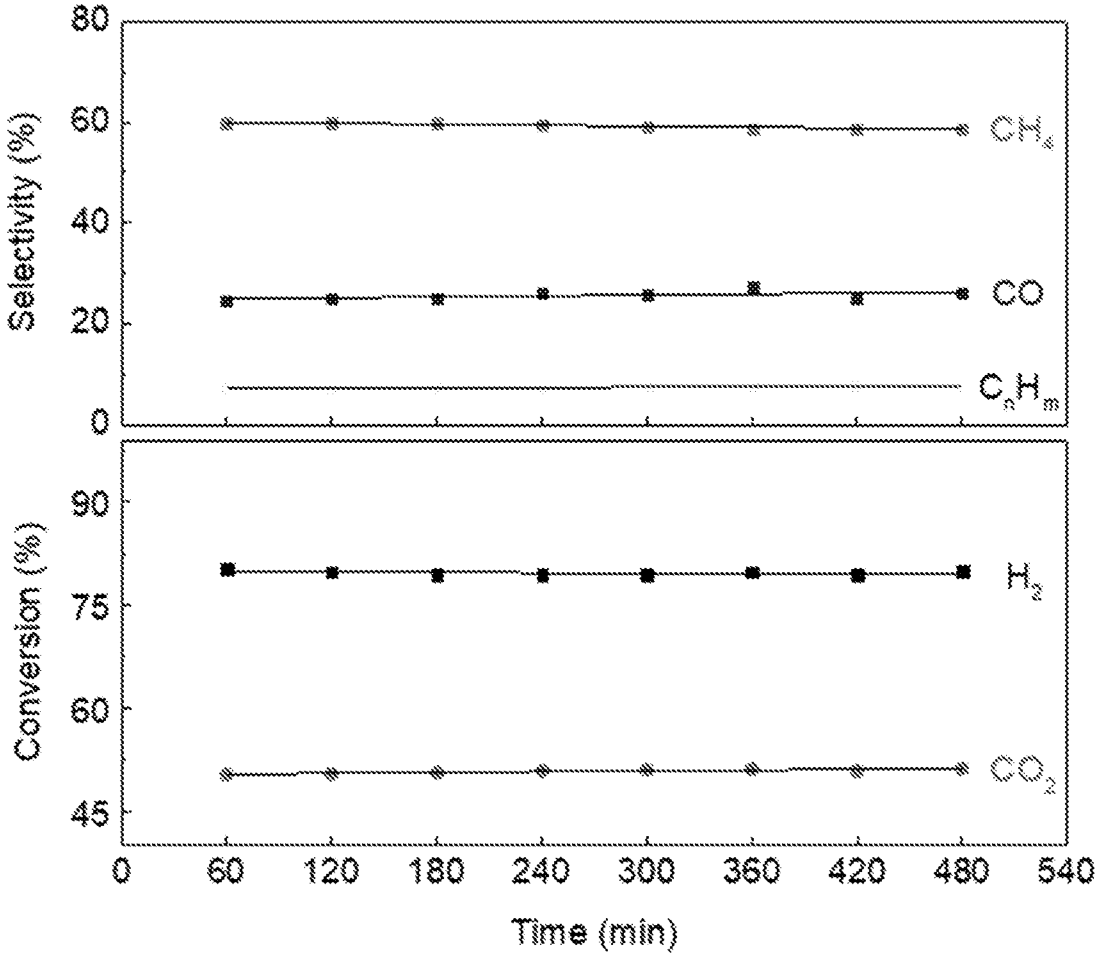
FIG. 8 shows reaction performance over the $NiMn/Al_2O_3$ catalyst as a function of time ($H_2/CO_2$=2:1, GHSV=2684 $h^{-1}$, 1 atm, SEI=57 kJ/L)

FIG. 8 shows reaction performance over the NiMn/$Al_2O_3$ catalyst as a function of time ($H_2$/$CO_2$=2:1, GHSV=2684 $h^{-1}$, 1 atm, SEI=57 kJ/L).

With the recent booming development of renewable technologies, the supply of hydrogen via water electrolysis has become economically available option (to some extent) and thus plasma-catalytic $CO_2$ methanation. In terms of energy efficiency of our work, the figures obtained with NiMn exceeded 0.4 mol/kWh. Thus, for each kWh supplied, more than 0.43 mol of carbon dioxide was converted and nearly 0.26 mol of $CH_4$ was produced, enhancing the $CH_4$ production achieved with plasma alone by a factor of 31.

Moreover, the stability of NiMn catalyst in the plasma under the same reaction conditions was investigated, as shown in FIG. 8. The high stability and effectively catalytic ability indicate that the carbon deposit and catalyst poisoning could be suppressed consummately. This low energy consumption technology makes it possible to produce synthetic $CH_4$ together with $CO_2$ emissions reduction without any additional heating or adiabatic apparatus, which could significantly reduce of negative investment and extend the service life of catalysts. Indeed, the flexibility of the production system allows the use of electrical energy produced off-peak (<30 €/MWh) or from the excess production coming from renewable sources, which is possible for an industrial scale.

TABLE 5

Summary of results for different catalysts.

| Catalyst | $CO_2$ Conversion (%) | $CH_4$ Selectivity (%) | $CH_4$ Yield (%) |
|---|---|---|---|
| Plasma only | 30.8 | 3.1 | 0.9 |
| $Al_2O_3$ | 33.5 | 3.1 | 1.0 |
| 1 wt % Mn/$Al_2O_3$ | 35.6 | 2.7 | 0.9 |
| Fe/$Al_2O_3$ | 28.7 | 2.8 | 0.8 |
| FeMn/$Al_2O_3$ | 28.5 | 2.6 | 0.7 |
| Cu/$Al_2O_3$ | 36.5 | 2.9 | 1.0 |
| CuMn/$Al_2O_3$ | 35.9 | 2.5 | 0.9 |
| Ni/$Al_2O_3$ | 44.8 | 45.3 | 20.2 |
| NiMn/$Al_2O_3$ | 50.3 | 59.7 | 30.0 |

In summary, our work further demonstrates that the combination of plasma and different catalysts offers very interesting opportunities for $CO_2$ methanation. The totally different catalytic ability and reaction mechanism in the plasma for Fe, Cu, Ni are significantly divergent from that in thermal catalysis field. Apart from Fe and Cu, the promoter Mn successfully enhanced the $CO_2$ conversion and $CH_4$ selectivity by the promotion the dispersion of Ni particles with the formation of smaller Ni sizes, the decrease of interaction effect between nickel and aluminum, and increment of weak-moderated basic sites for carbon oxide species adsorption. The excellent performance of NiMn catalyst coupling with the plasma makes it possible to obtain high $CH_4$ yield by less energy consumption (electrical and hydrogen supply) without any other heating equipment.

Example 3: 7 wt. % Ni/1 wt. % X/$Al_2O_3$ (X=Zr, Mg, Ce, Mn) Catalysts $Al_2O_3$ supported 7 wt. % Ni and 1 wt. % promoters (Zr, Mg, Ce, Mn) were prepared using an incipient wetness impregnation technique. In a typical procedure, the metal precursors of nitrate hydrate for nickel (II), zirconium(IV), magnesium(II), cerium(III) and manganese (II) were dissolved in 4.8 mL of deionized water. The solution was then added dropwise to 2 g of γ-$Al_2O_3$ (Aladdin, 40-60 mesh) and mixed. The impregnated samples and pure $Al_2O_3$ were dried overnight in the air, with further dehydration in the oven at 120° C. for 4 h, then transferred to a muffle furnace to be calcined at 450° C. for 5 h. The calcined catalysts were pre-reduced under the mixed gas of 20 mL/min $H_2$ and 30 mL/min Ar at 600° C. for 5 h before the reaction. The obtained catalysts were labeled as NiXAl (X=Zr, Mg, Ce and Mn).

Figure 9A:
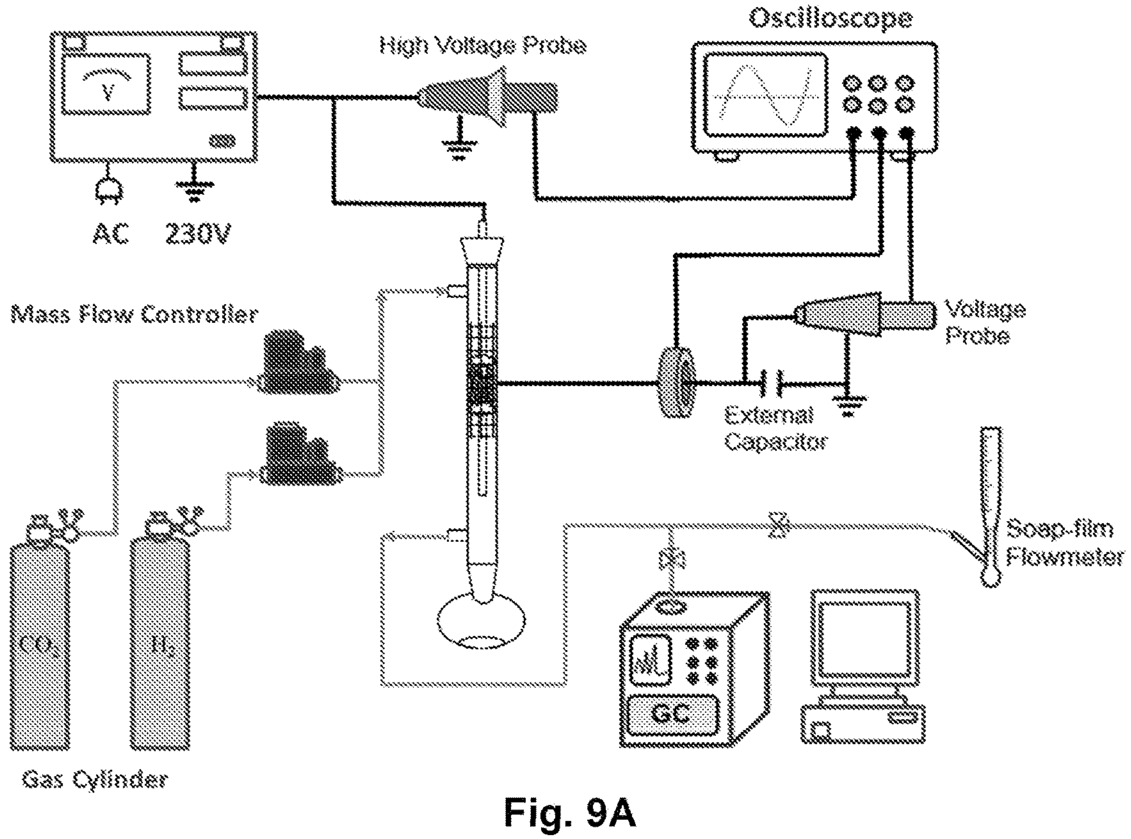
FIG. 9A schematically depicts the experimental setup.
Figure 9B:
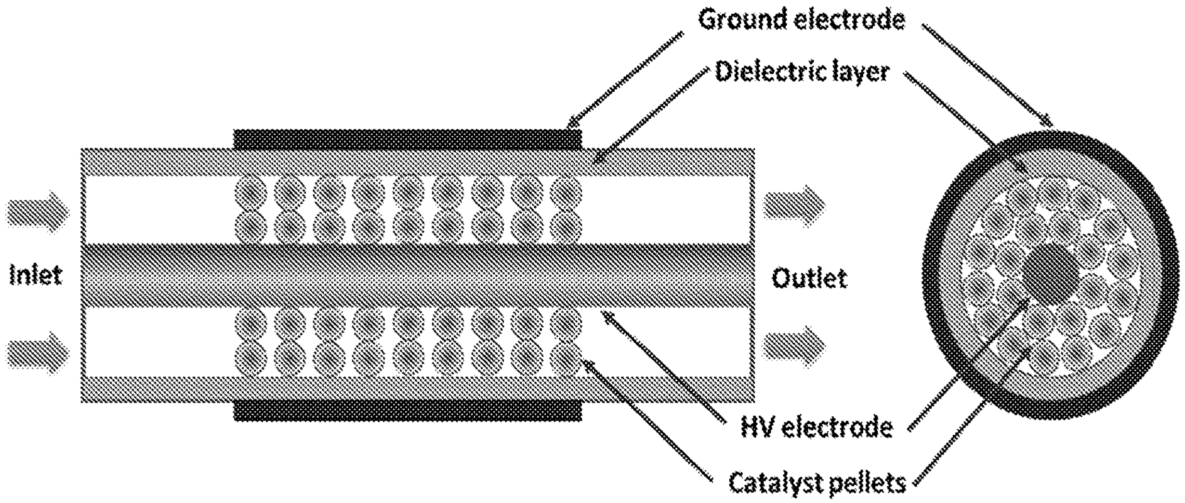
FIG. 9B schematically depicts an axial cross-section and a transverse cross-section of a DBD reactor.

The performance of the catalysts for $CO_2$ hydrogenation was evaluated in a coaxial DBD reactor, same to in Example 1. As is shown in FIG. 9B, a 6 cm long stainless-steel mesh was wrapped outside the quartz tube (6 mm i.d.), acting as a ground electrode through an external capacitor $C_{ext}$ (0.47 μF). The inner high voltage electrode was a stainless-steel rod (diameter 2 mm), fixed in the center of the quartz tube. The DBD reactor was supplied by a high voltage AC power supply with a maximum peak voltage of 30 kV and a frequency of 5-20 kHz. All the catalysts (0.5 g) were packed into the center of the plasma reactor discharge area. $H_2$ and $CO_2$ were used as reactant gases. The discharge power was calculated using the Lissajous method. Besides, an online power measurement system was used to monitor the discharge power of the DBD reactor in real-time. The specific energy input (SEI) was controlled from 1 kJ/L to 19 kJ/L.

Catalyst: 0.5 g; 40-60 mesh; packing length 4 cm; reaction temperature: 125-155° C.

During the $CO_2$ hydrogenation reactions, the gas products were quantified with a gas chromatograph (Agilent GC 7820A) equipped with a flame ionisation detector (FID) and a thermal conductivity detector (TCD). Each measurement was repeated three times and had a high reproducibility with a measurement error of less than 1%.

TABLE 6

| Physical properties of the fresh catalysts (after reduction) | |
|---|---|
| Catalysts | Surface area ($m^2/g$) [a] |
| $Al_2O_3$ (comp) | 206 |
| NiAl | 141 |
| NiZrAl | 175 |
| NiMgAl | 170 |
| NiCeAl | 173 |
| NiMnAl | 158 |

[a] Measured by $N_2$-adsorption

The values of specific BET surface area of the reduced catalysts are listed in Table 6.

The bare $\gamma$-$Al_2O_3$ supporter exhibits a surface area of 206 $m^2/g$ which is larger than other loaded catalysts (from 141 to 175 $m^2/g$). This may be due to the blocking of pore structures. However, by the addition of promoters, the surface areas grow with respect to single-metal catalysts, which result from the suppression of agglomeration during the reduction process. Despite these delicate differences, the physical properties of the catalysts are quite similar to each other, irrespective of what kind of promoters are used.

Figure 10A:
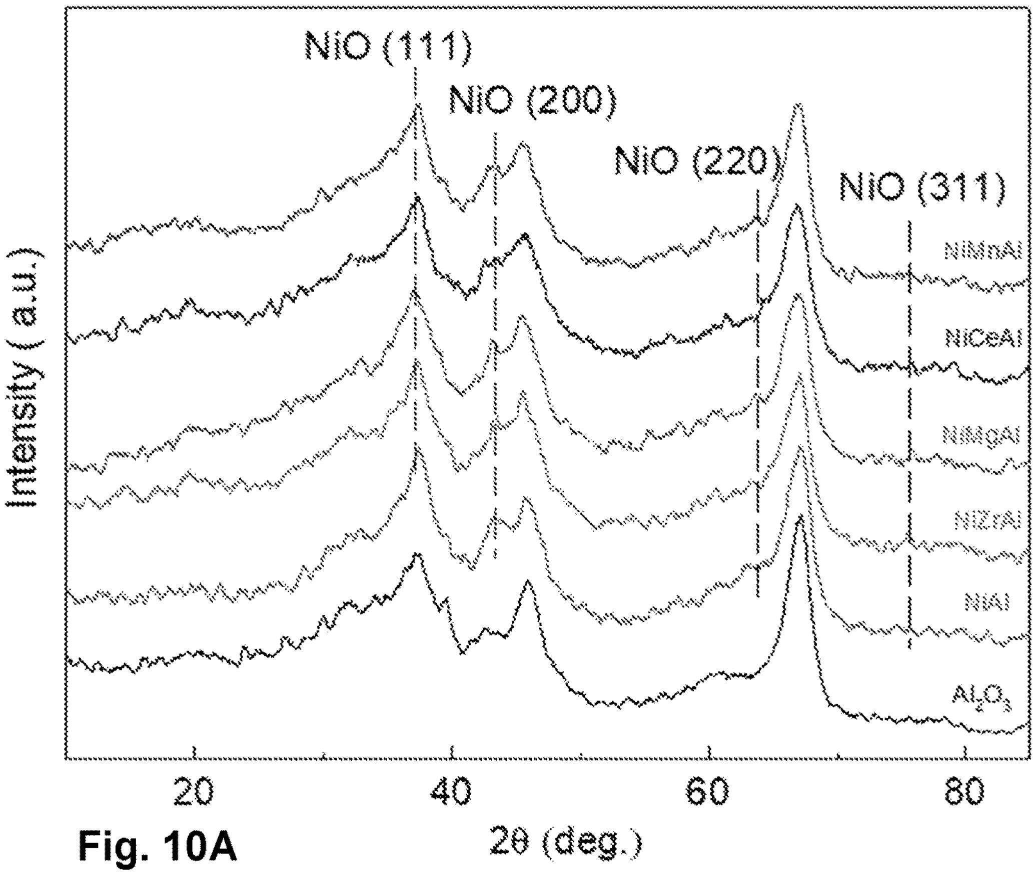
FIG. 10A shows XRD patterns of the fresh catalysts after calcination.
Figure 10B:
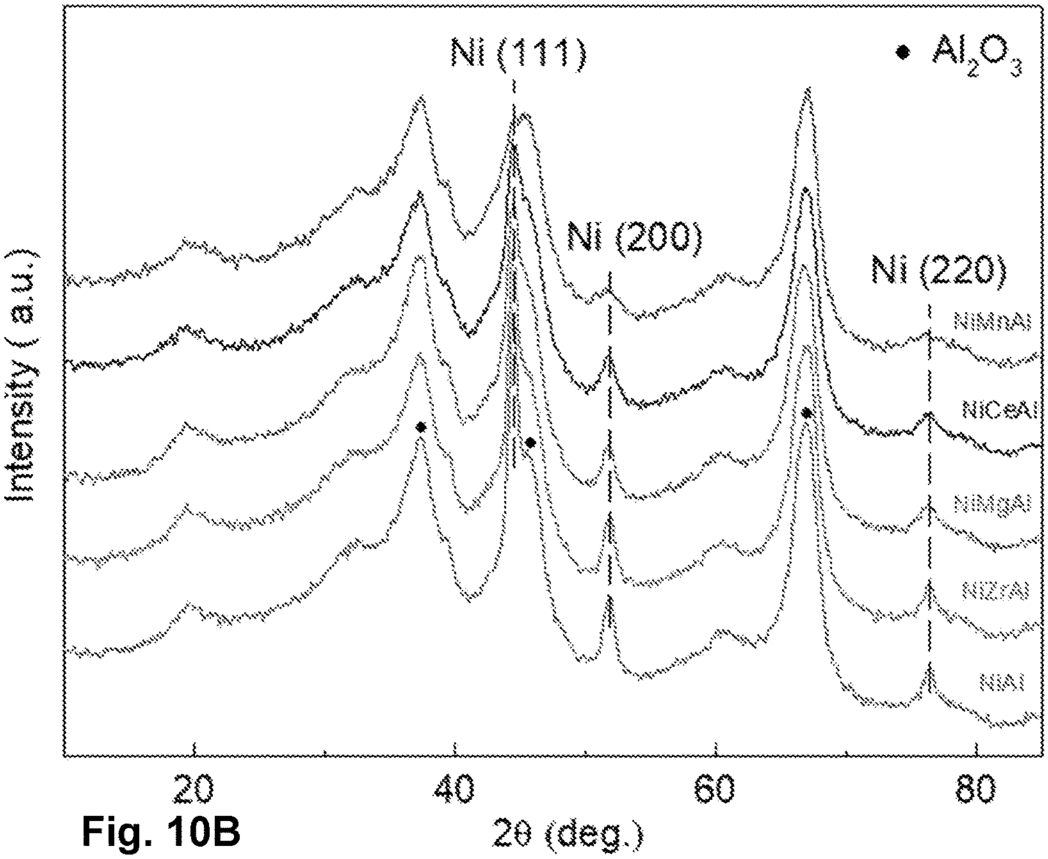
FIG. 10B shows XRD spectra of the fresh catalysts after reduction.
Figure 10C:
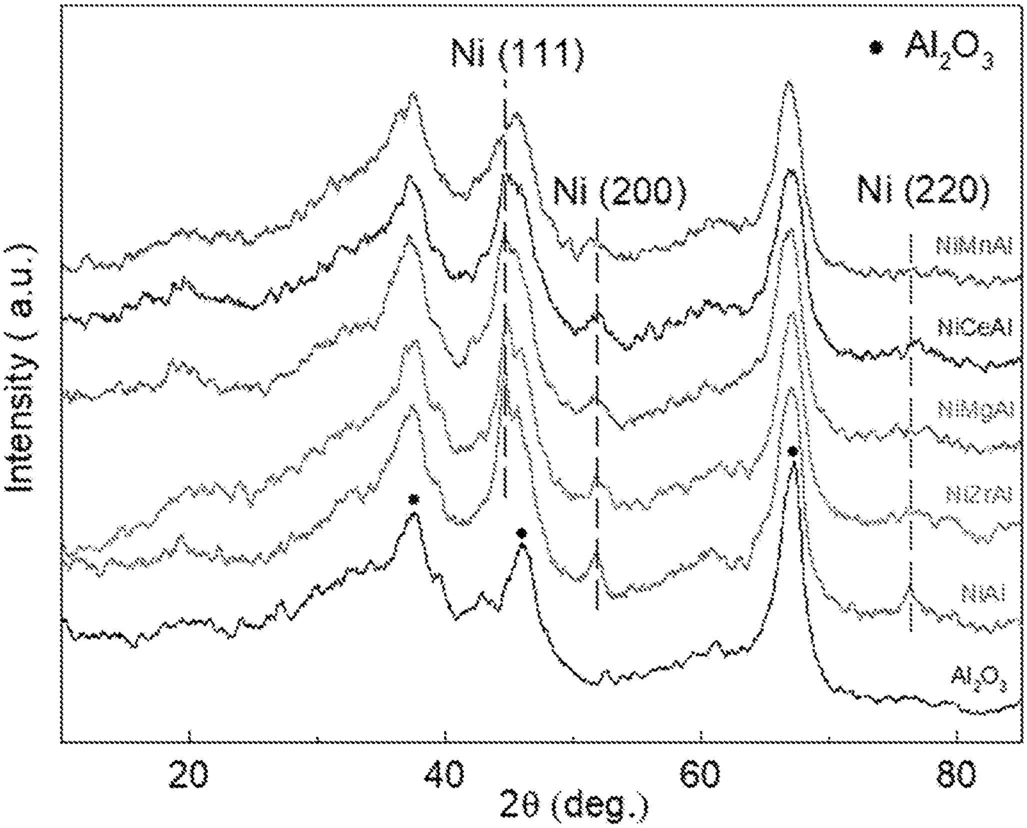
FIG. 10C shows XRD patterns of the spent catalysts.

The crystallite structures of the calcined, reduced and spent catalysts are presented in FIGS. 10A to 10C, respectively. The diffraction pattern of $Al_2O_3$ has several peaks that can be well-indexed to $\gamma$-$Al_2O_3$(JCPDS10-0425). According to the XRD patterns of the catalysts before the reduction, only weak and inconspicuous NiO characteristic peaks at 37.2°, 43.3° and 62.9° (JCPDS47-1049) were detected among the Ni-based catalysts. After being reduced at 600° C., the metallic Ni characteristic peaks in 44.5°, 51.8° and 76.4° (JCPDS65-2865), corresponding to the Ni (111), (200) and (220) crystal planes respectively, were evidently confirmed on the catalysts. It is interesting to note that the metal diffraction peaks become weaker and broader, which indicates that the particles on the support are smaller and evenly distributed. Furthermore, after Mn was added to the Ni-based catalyst, the characteristic diffraction peaks of neither Mn nor Ni could be observed because of the weak crystallization and suppression of agglomeration during the high-temperature reduction process. After the reaction, the characteristic peaks in FIG. 10C exhibiting the same position and trend indicate the stability of the catalysts during the plasma discharge.

Figure 11A:
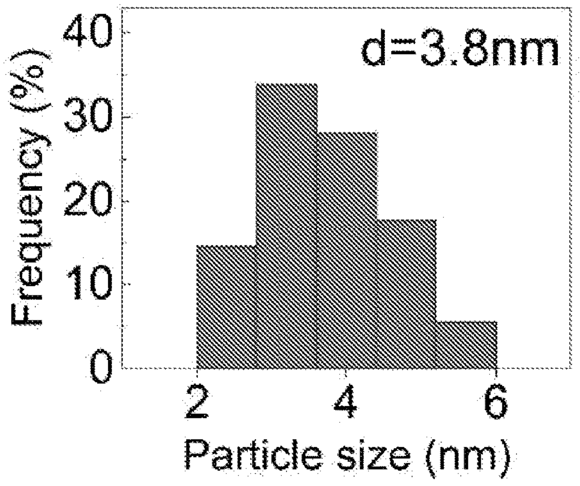
FIGS. 11A to 11D show metal particle size distributions on fresh catalysts after reduction.
Figure 11B:
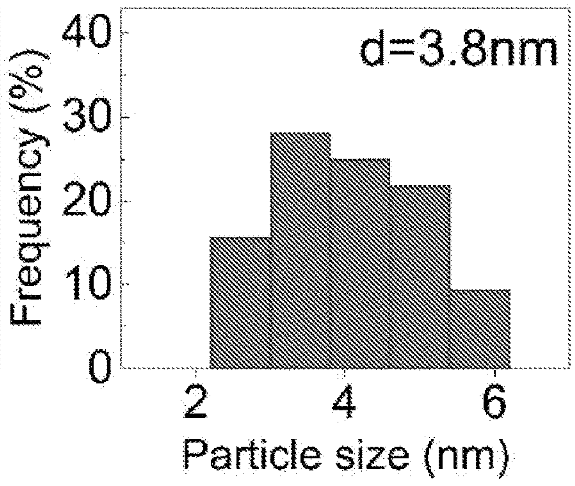
Figure 11C:
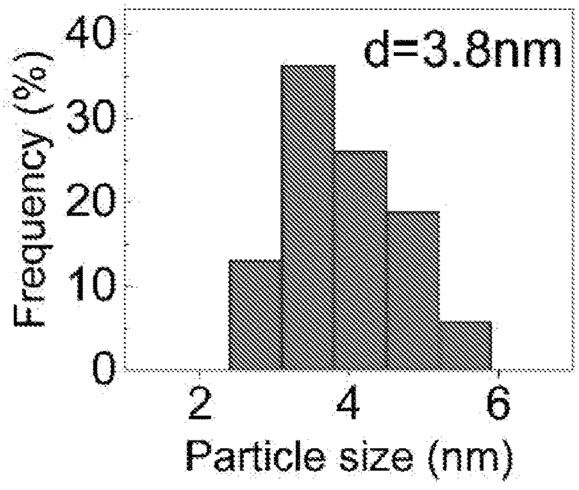
Figure 11D:
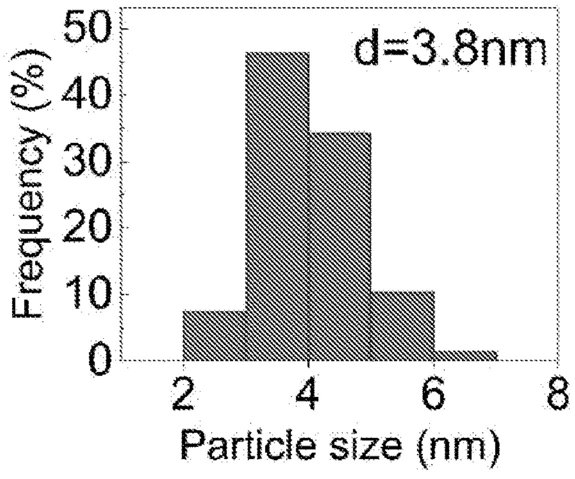

FIGS. 11A to 11D show metal particle size distributions on fresh catalysts after reduction; FIG. 11A NiZrAl; FIG. 11B NiMgAl; FIG. 11C NiCeAl; and FIG. 11D NiMnAl.

TABLE 7

| Chemical properties of the catalysts | | | |
|---|---|---|---|
| Catalysts | $H_2$ consumed (mmol/g) [b] | $CO_2$ desorbed (mmol/g) [c] | Ni/Al (%) [d] |
| $Al_2O_3$ (comp) | — | 2.55 | — |
| NiAl | 0.43 | 2.24 | 2.70 |
| NiZrAl | 0.46 | 2.18 | 2.57 |
| NiMgAl | 0.48 | 2.51 | 2.48 |
| NiCeAl | 0.48 | 2.30 | 2.94 |
| NiMnAl | 0.51 | 1.80 | 3.79 |

a. Calculated via $H_2$-TPR analysis of the fresh catalysts after calcination
[b] Calculated via $CO_2$-TPD analysis of the fresh catalysts after reduction
[c] Calculated via XPS analysis of the fresh catalysts after reduction Effect of 7 wt. % Ni/1 wt. % X/$Al_2O_3$ Catalyst (X=Zr, Mg, Ce, Mn)

The NiMnAl (7 wt. % Ni/1 wt. % Mn/$Al_2O_3$) catalyst shows the best performance: highest conversion of $CO_2$ (~87%) and highest methane selectivity of 99%. Investigated in various gas ratio, gas flow rate and discharge power, this catalyst shows the highest space time yield of $CH_4$ for 1500 $\mu mol/g_{Ni}/s$. It is also very stable after running the reaction for 8 hours.

1. Performance at Low Flow Rate
   - Specific energy input (SEI): 5-19 kJ/L; discharge power=8.5 W
   - Gas: $H_2/CO_2$=4:1 (total 30-100 ml/min); gas hourly space velocity (GHSV) 1792-5971 $h^{-1}$
   - Catalyst: 0.5 g; 40-60 mesh; packing length 4 cm; reaction temperature: 125-155° C.

Figure 12A:
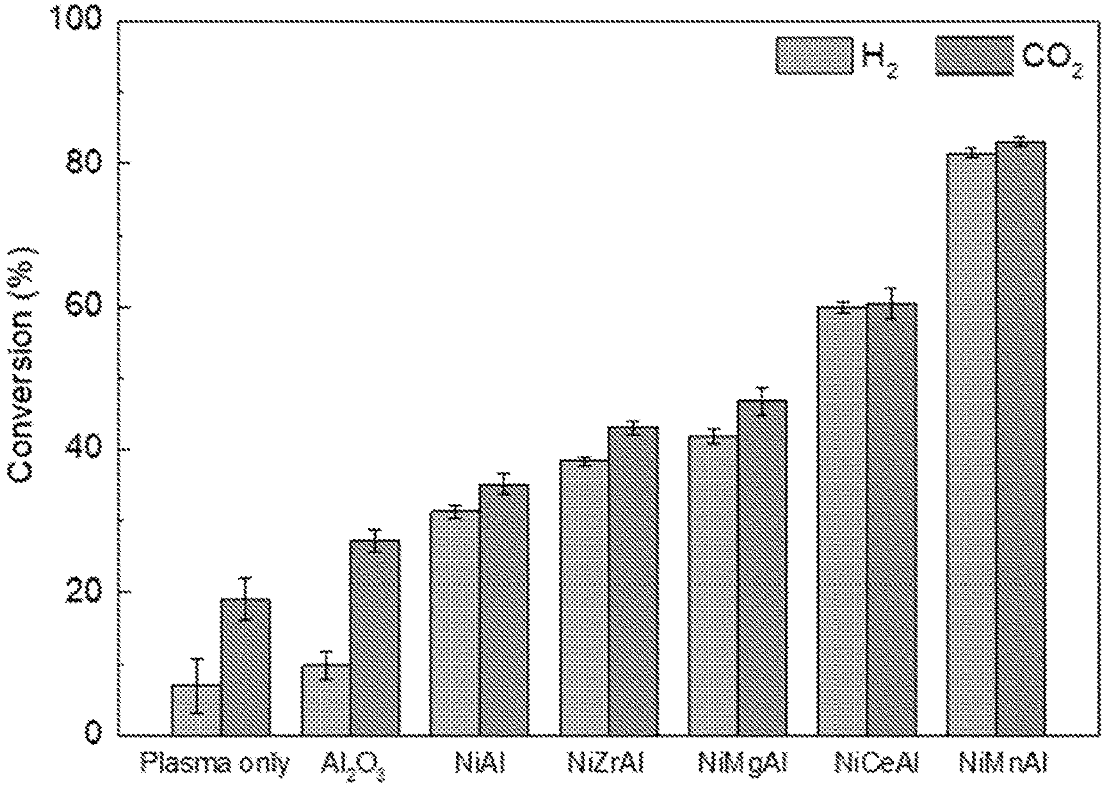
FIG. 12A shows conversions of $CO_2$ and $H_2$.
Figure 12B:
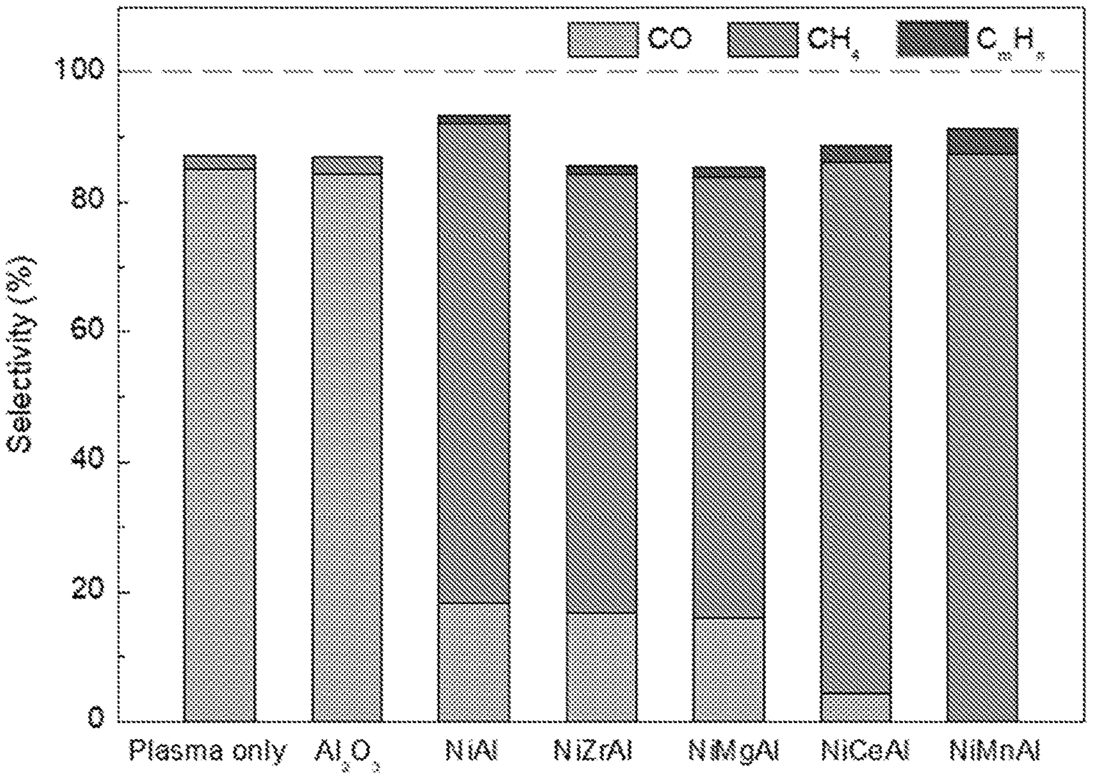
FIG. 12B shows selectivity of gas products.
Figure 12C:
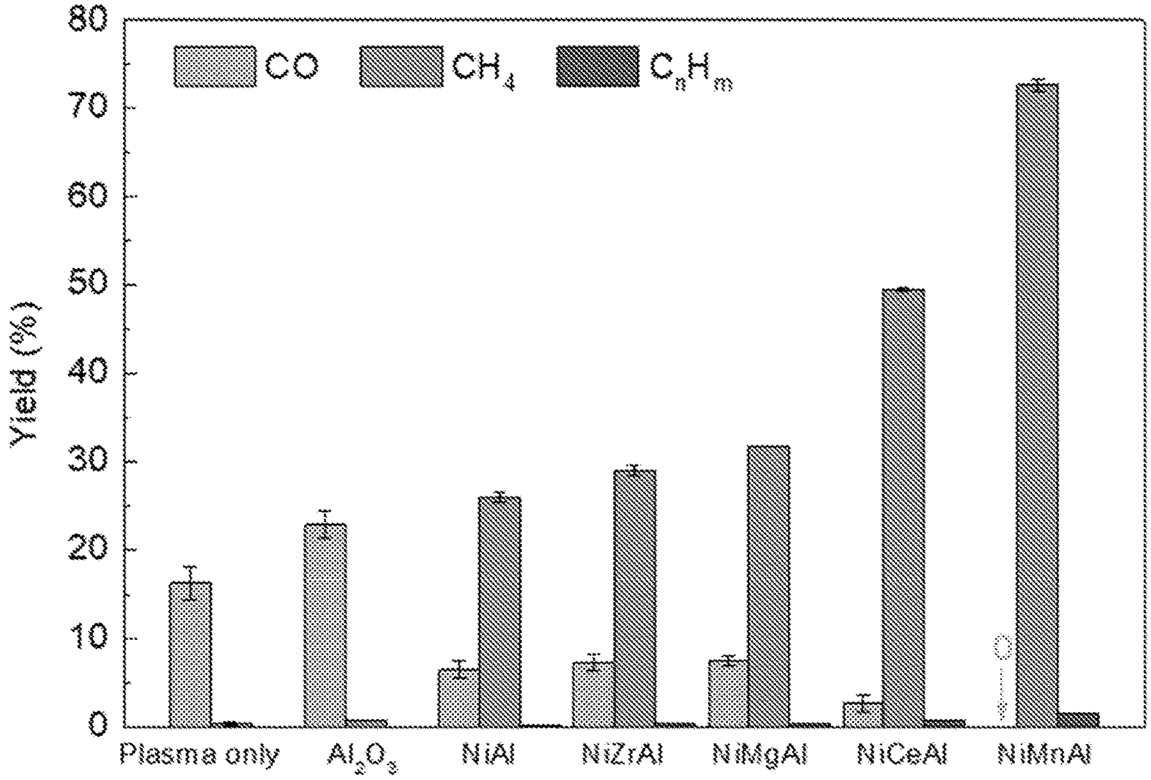
FIG. 12C shows yield of gas products ($H_2/CO_2$=4:1, GHSV=1792 $h^{-1}$, 1 atm)
Figure 12D:
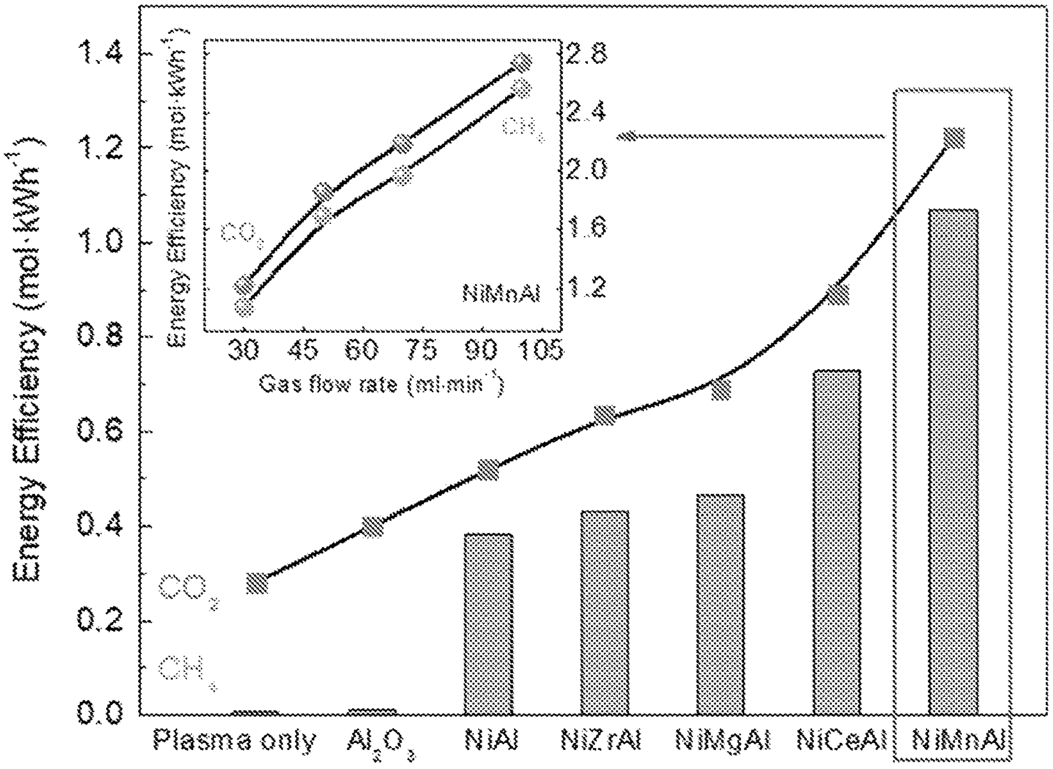
FIG. 12D shows energy efficiency for $CO_2$ conversion and $CH_4$ production at different gas flow rates.
Figure 13:
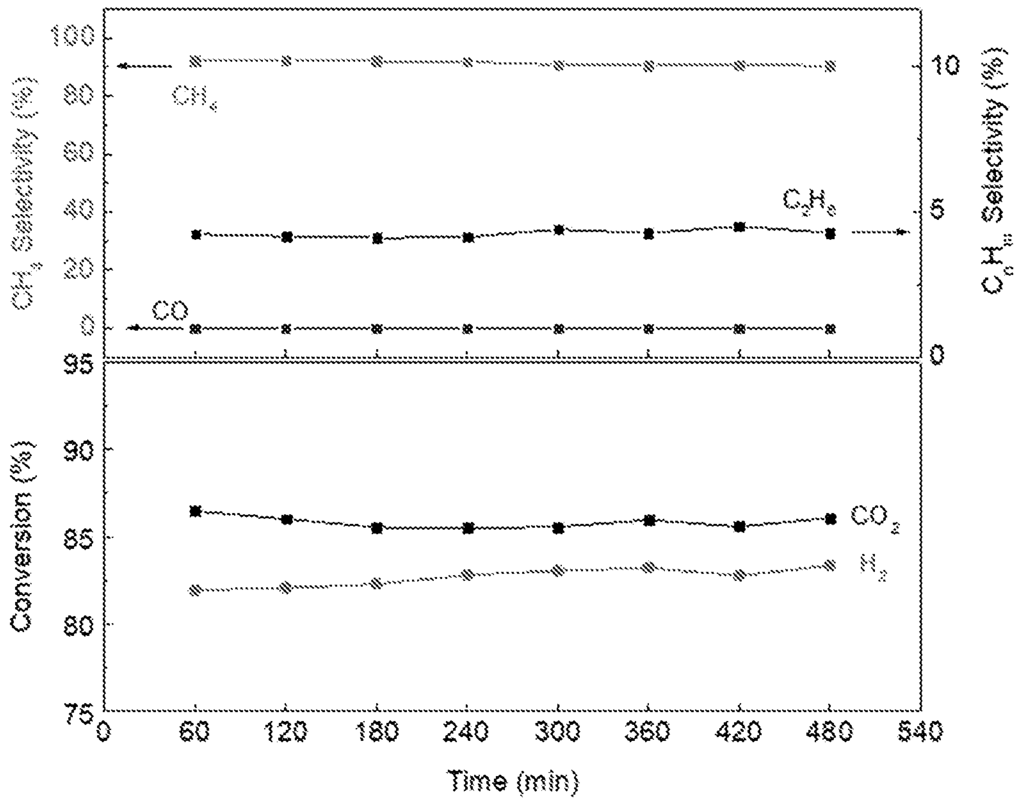
FIG. 13 shows $CO_2$ conversion and products selectivities over NiMnAl as a function of time.

FIG. 12A shows conversion of $CO_2$ and $H_2$; FIG. 12B shows selectivity of gas products; FIG. 12C shows yield of gas products; and FIG. 12D shows energy efficiency for $CO_2$ conversion and $CH_4$ production at different gas flow rates.

FIG. 12A shows $CO_2$ and $H_2$ conversion on the $Al_2O_3$ and metal-loaded catalysts under the plasma activation. The temperature of the reaction was 125-155° C. when the reaction reaches stability. For comparison, all of the catalysts were investigated for $CO_2$ hydrogenation under the same experimental conditions at 150° C. without plasma. However, no conversion could be initiated by thermal catalysis.

As is shown in FIG. 12A, in the presence of plasma, promoters have different levels of improvement for the methanation process, while only 19% of $CO_2$ converted in the absence of a catalyst. Under plasma assistance, the $CO_2$ conversions for the catalysts follow the order: plasma alone<$Al_2O_3$<NiAl<NiZrAl<NiMgAl<NiCeAl<NiMnAl. Interestingly, as to NiMnAl, the considerable increment of $H_2$ and $CO_2$ conversions were encountered, reaching nearly 83% for $CO_2$ while surpassing 81% in the case of $H_2$.

As presented in FIG. 12B, the product selectivities were also significantly affected combining with the catalysts. For the plasma only and aluminum oxide, the $CO_2$ molecules dissociated directly to CO via the collision of electrons in the plasma. Moreover, the $CH_4$ selectivity (around 74% for NiAl) was further enhanced by the addition of Mn reaching a maximum of 88%. In this case, $CH_4$ became the dominated product.

In terms of methane energy efficiency, the figures (FIG. 12C) obtained with NiMnAl exceeded 2.7 mol/kWh, which had achieved in particular for plasma alone by a factor of 423. Then the NiMnAl catalyst packed in the plasma was investigated by varying the total flow rate with a constant $H_2/CO_2$ ratio and discharge power. The EE for both $CO_2$ and $CH_4$ increases to 2.5 times when the flow rate rises to 100 ml/min. Moreover, the stability of NiMnAl catalyst was investigated both in the continuous plasma and over 5 cycles, as shown in FIG. 12D. The high stability and effectively catalytic ability of this catalyst within the plasma indicated that the undesirable carbon deposit and catalyst poisoning from the C, CO and $H_2O$ during the reaction could be suppressed consummately. This low energy consumption technology makes it possible to produce synthetic $CH_4$ together with $CO_2$ emissions reduction without any additional heating or adiabatic apparatus, which could significantly help negative investment with the service life of the catalyst extended.

2. Performance at High Flow Rate

Specific energy input (SEI): 0.5-17 kJ/L; discharge power=5-10 W;

Gas: $H_2/CO_2$=4:1 (total 30-500 ml/min); gas hourly space velocity (GHSV) 2090-29857 $h^{-1}$ Catalyst: 0.5 g; 40-60 mesh; packing length 4 cm; reaction temperature: 125-155° C.

Figure 14A:
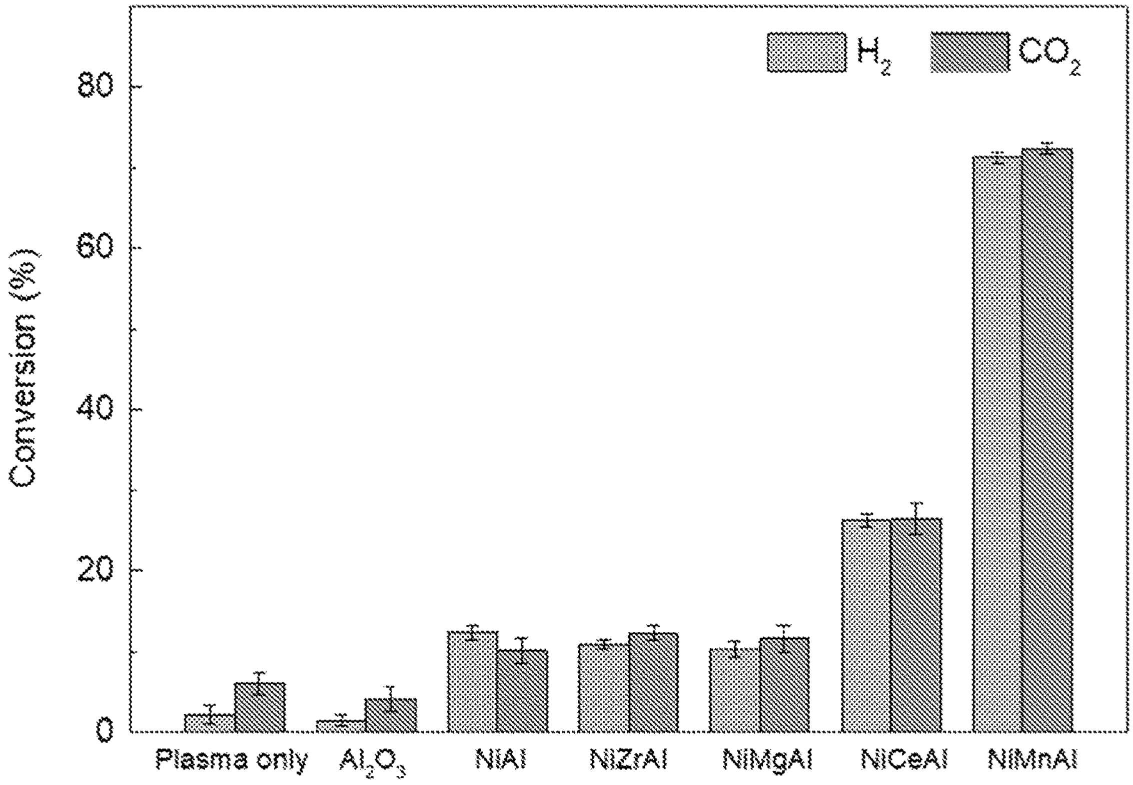
FIG. 14A shows conversions of $H_2$ and $CO_2$.
Figure 14B:
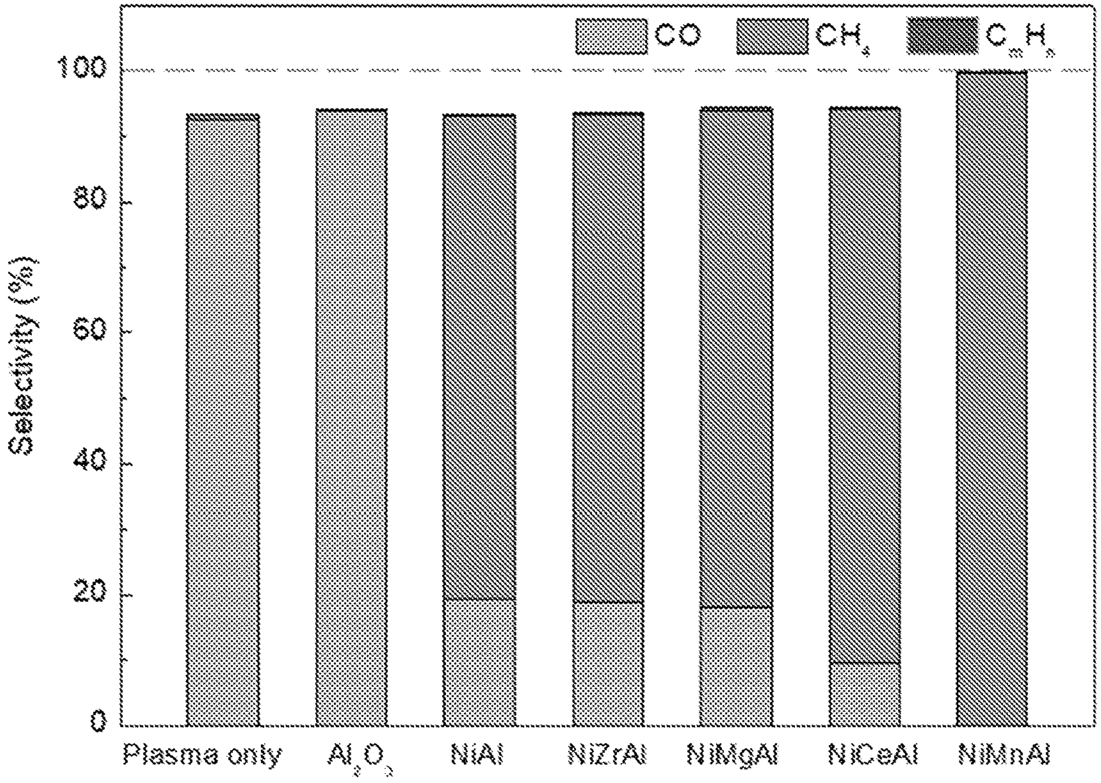
FIG. 14B shows selectivity of gas products.
Figure 14C:
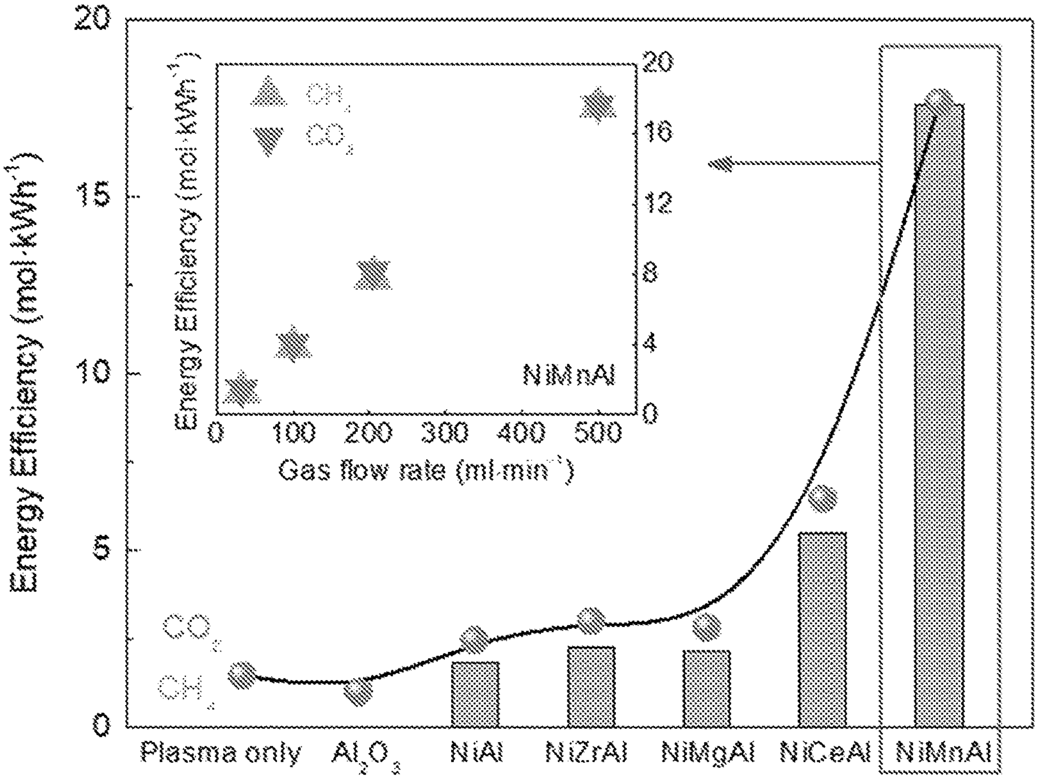
FIG. 14C shows energy efficiency for $CO_2$ conversion and $CH_4$ production at different gas flow rates.
Figure 14D:
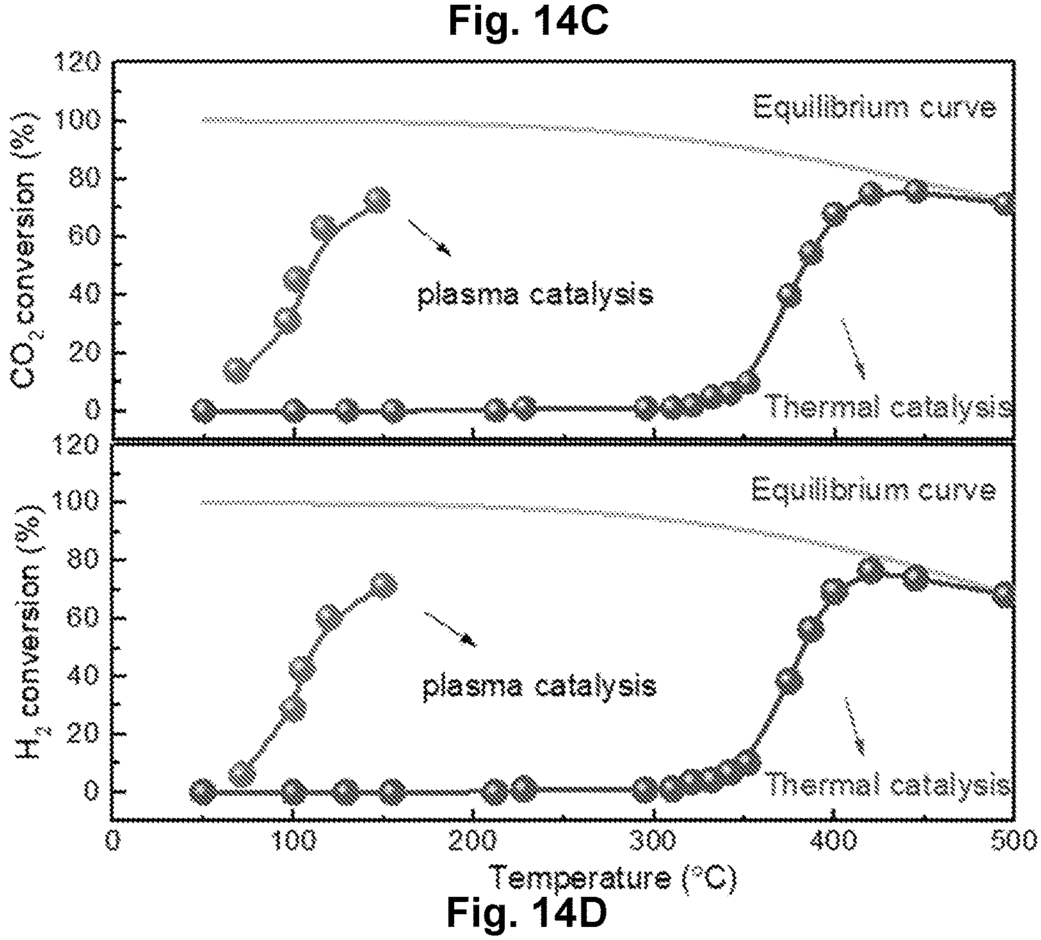
FIG. 14D shows conversion of $H_2$ and $CO_2$ at different reaction temperatures over NiMnAl ($H_2/CO_2$=4:1, GHSV=29857 $h^{-1}$, 1 atm)
Figure 14E:
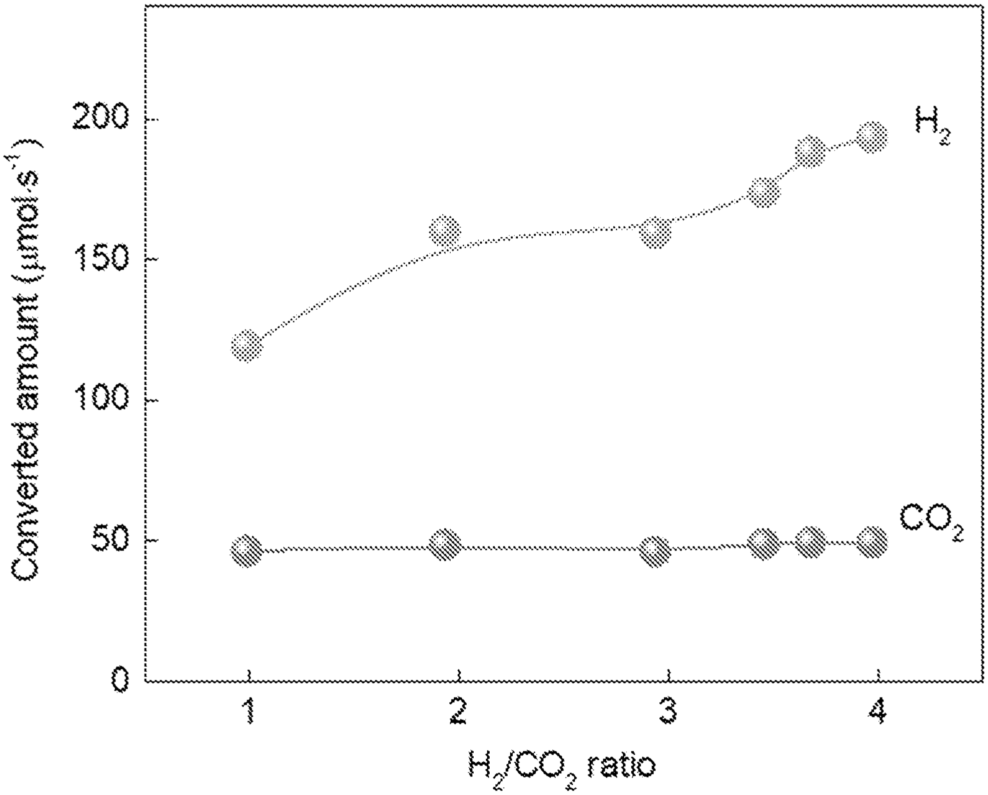
FIG. 14E shows the converted amounts of $CO_2$ and $H_2$ over NiMnAl at different $H_2/CO_2$ molar ratios (GHSV=29857 $h^{-1}$, 1 atm, SEI=1.2 kJ/L)

FIG. 14A shows conversion of $H_2$ and $CO_2$; FIG. 14B shows selectivity of gas products; FIG. 14C shows energy efficiency for $CO_2$ conversion and $CH_4$ production at different gas flow rates; FIG. 14D shows conversion of $H_2$ and $CO_2$ at different reaction temperatures over NiMnAl ($H_2/CO_2$=4:1, GHSV=29857 $h^{-1}$, 1 atm); and FIG. 14E shows the converted amounts of $CO_2$ and $H_2$ over NiMnAl at different $H_2/CO_2$ molar ratios (GHSV=29857 $h^{-1}$, 1 atm, SEI=1.2 kJ/L).

FIG. 14A shows $CO_2$ and $H_2$ conversion on the bare $Al_2O_3$ and metal-loaded catalysts under the plasma activation. For comparison, all of the catalysts were investigated under the same experimental conditions at 180° C. without plasma. However, no conversion could be initiated by the thermal catalysis.

As is shown in FIG. 14A, in the presence of plasma, promoters have different levels of improvement for the methanation process, while only 6% of $CO_2$ converted in the absence of a catalyst at a high gas flow rate. Under plasma assistance, the $CO_2$ conversions for the catalysts follow the order: $Al_2O_3$<plasma alone<NiAl<NiZrAl<NiMgAl<NiCeAl<NiMnAl. Most catalysts have a significant conversion decrease due to the increased gas flow rate, which could reduce the reaction residence time. Interestingly, as to NiMnAl, $H_2$ and $CO_2$ conversions were still substantial, reaching nearly 75% for $CO_2$ while surpassing 70% in the case of $H_2$.

As presented in FIG. 14B, the product selectivities were also significantly affected combining with the catalysts. For the plasma only and aluminum oxide, the $CO_2$ molecules dissociated directly to CO. Moreover, the $CH_4$ selectivity (around 74% for NiAl) was further enhanced by the addition of Mn reaching a maximum of 99.6%. In this case, $CH_4$ became the dominated product.

Figure 15A:
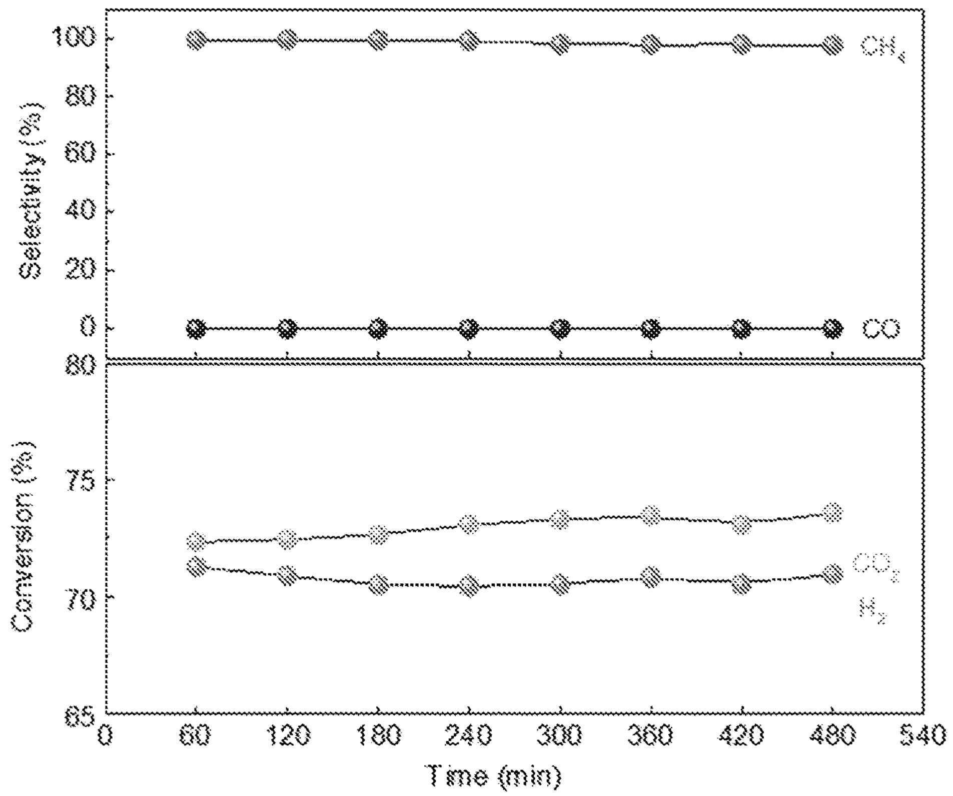
FIG. 15A shows $CO_2$ conversion and products selectivities over NiMnAl as a function of time.
Figure 15B:
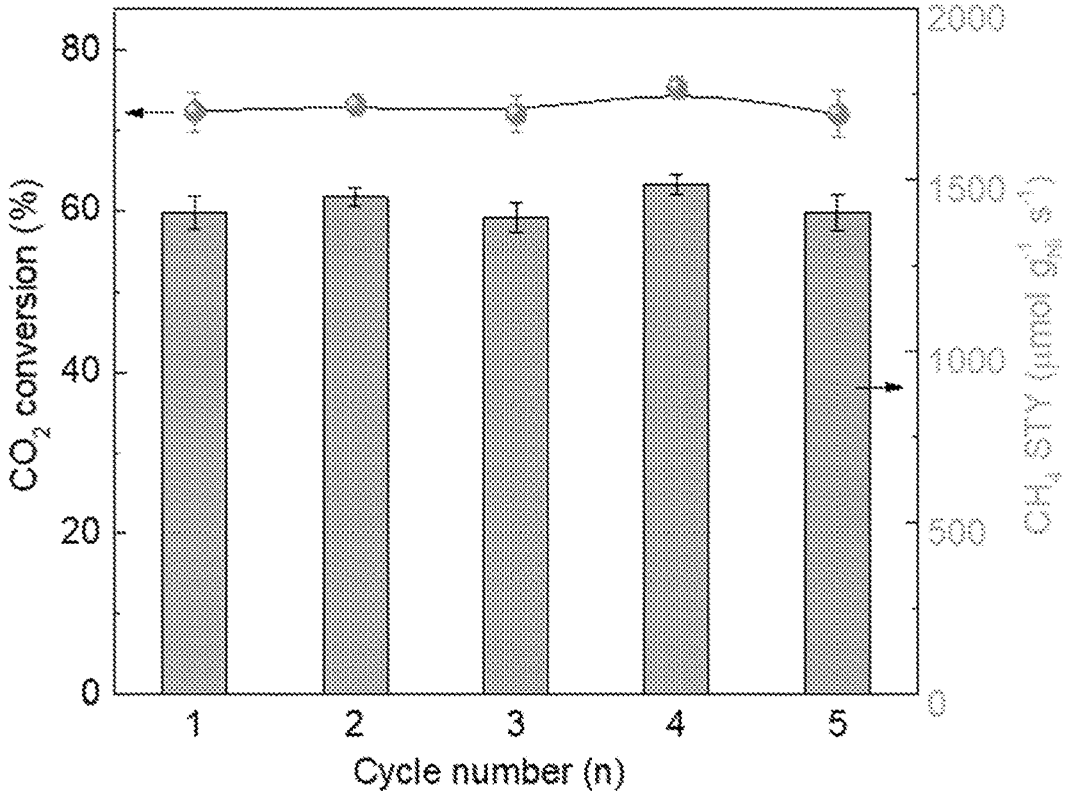
FIG. 15B shows $CO_2$ conversion and $CH_4$ space time yield (STY) versus recycle times over NiMnAl ($H_2/CO_2$=4:1, GHSV=29857 $h^{-1}$, 1 atm, SEI=1.2 kJ/L)

In terms of the energy efficiency for methane production, the figures (FIG. 14C) obtained with NiMnAl exceeded 17.7 mol/kWh, which had achieved in particular for plasma alone by a factor of 1397. Then the NiMnAl catalyst packed in the plasma was investigated by varying the total flow rate with a constant $H_2/CO_2$ ratio and discharge power. The EE for both $CO_2$ and $CH_4$ is increased by 13 times when the flow rate rises to 500 ml/min. Moreover, the stability of the NiMnAl catalyst was investigated both in the continuous plasma and over 5 cycles, as shown in FIGS. 15A and 15B. The high stability and catalytic activity of this catalyst within the plasma indicated that the undesirable carbon deposit and catalyst poisoning from the C, CO and $H_2O$ during the reaction could be suppressed consummately.

This low energy consumption technology makes it possible to produce synthetic $CH_4$ together with $CO_2$ emissions reduction at a more flexible reaction condition. Comparing with other promoters at the higher gas low rate, the excellent performance of NiMnAl catalyst coupling with the plasma makes it possible to obtain high $CH_4$ yield by less energy consumption (electrical and hydrogen supply) without any other heating or adiabatic equipment. Indeed, the flexibility of the production system allows the use of electrical energy produced off-peak (<30 €/MWh) or from the excess production coming from renewable sources, which strengthens the prospects for commercial application.

Example 4: 7 wt. % Ni/1 wt. % $Mn/Al_2O_3$ Catalyst (NiMnAl)

Figure 16:
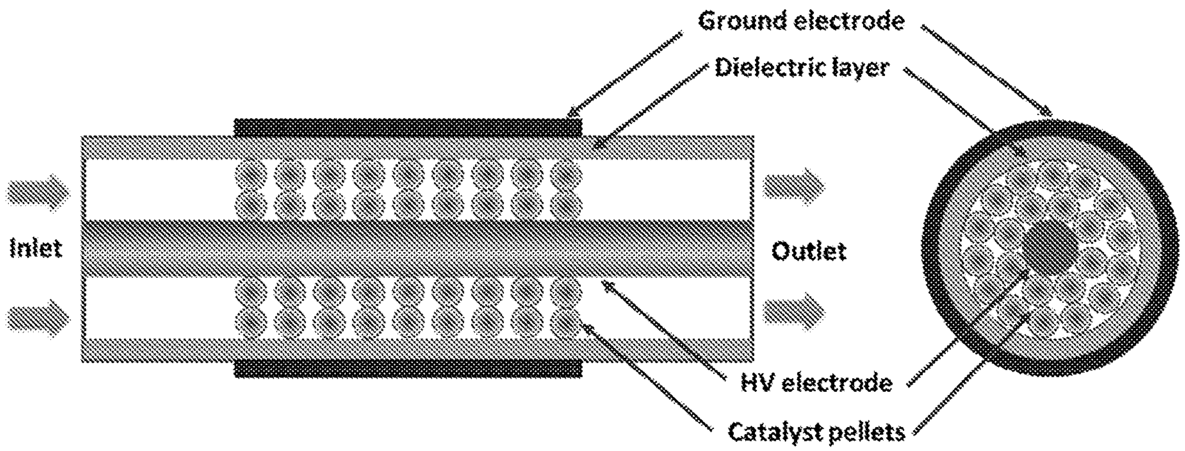
FIG. 16 schematically depicts an axial cross-section and a transverse cross-section of a big DBD reactor.

The NiMnAl catalyst (7 wt. % Ni/1 wt. % $Mn/Al_2O_3$) was also tested in a scaled-up DBD reactor (with a larger dimension and discharge volume) for plasma-catalytic $CO_2$ methanation at 1 atm. As is shown in FIG. 16, a coaxial DBD reactor was employed in this study. An 8 cm long stainless-steel mesh was wrapped outside a quartz tube (inner diameter 22 mm, outer diameter 25 mm) and was grounded through an external capacitor $C_{ext}$(0.47 μF). A stainless-steel rod (outer diameter 16 mm) was fixed in the centre of the quartz tube as the high voltage electrode. The discharge gap was 3 mm. The DBD reactor was connected to a high voltage AC power supply. No additional heating or cooling was used for this DBD reactor. The discharge power was 30 W or 40 W. The SEI was controlled from 10 kJ/L to 60 kJ/L. Catalyst (5.8 g, catalyst particle size 40-60 mesh, packing length 8 cm) was packed in the center of the discharge area. $H_2$ and $CO_2$ were used as reactant gases at a $H_2/CO_2$ molar ratio of 4:1 and a total flow rate of 30-200 ml/min. The GHSV was 100-900 $h^{-1}$. The reaction temperature was 125-175° C.

Figure 17:
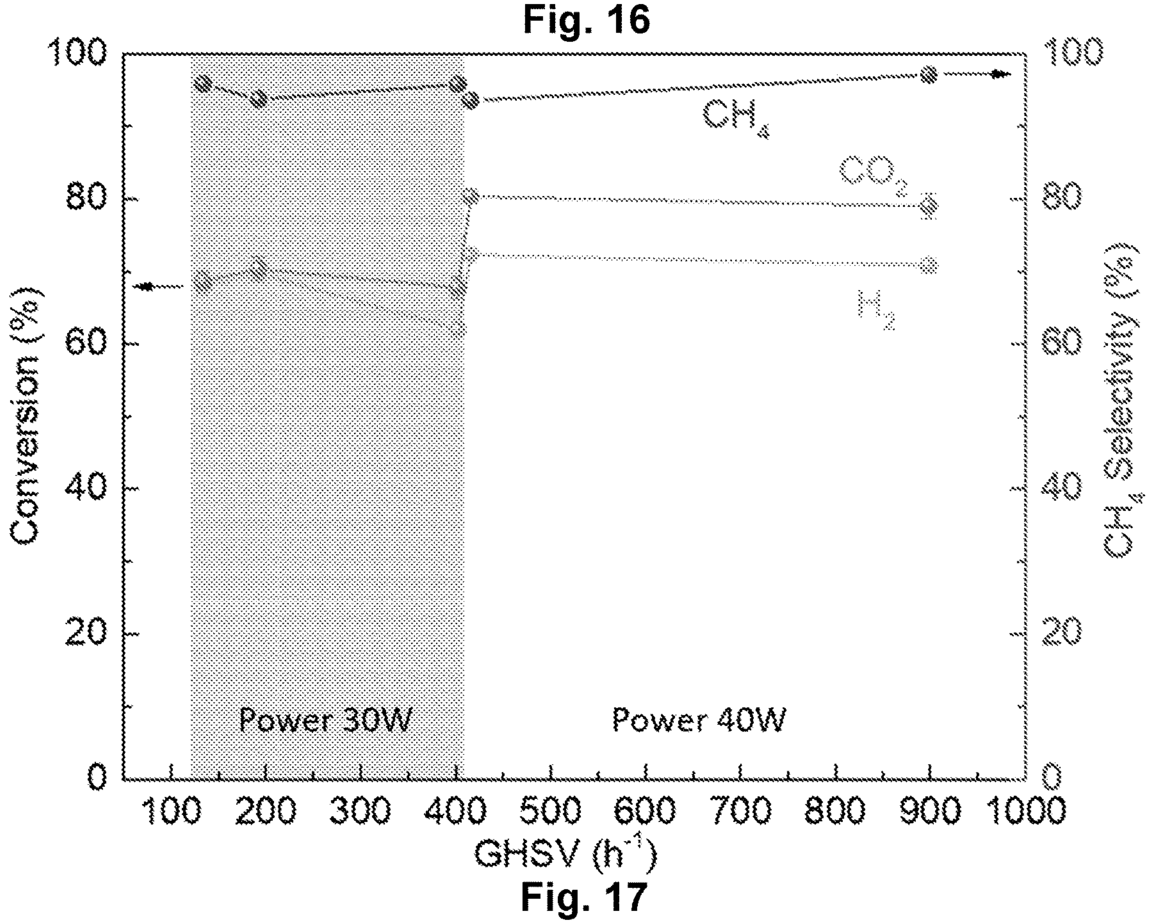
FIG. 17 shows conversions of $H_2$ and $CO_2$, and selectivity of $CH_4$ at different gas hourly space velocity (GHSV, $h^{-1}$) and different discharge powers over NiMnAl ($H_2/CO_2$=4:1, GHSV=100-900 $h^{-1}$, power=30-40 W, 1 atm).

FIG. 17 shows the reaction performance of plasma-catalytic $CO_2$ methanation using the NiMnAl catalyst in a scaled-up DBD reactor. Compared to the same catalyst used in Example 3, similar $CO_2$ conversions and $CH_4$ selectivity were achieved using the scaled-up reactor. At a total flow rate of 30 ml to 90 ml/min (GHSV 134-402 $h^{-1}$), the highest $CO_2$ conversion was 68% at a discharge power of 30 W. At a discharge power of 40 W, the highest $CO_2$ conversion (79%) and $CH_4$ selectivity (97%) were achieved at a high total gas flow rate of 200 ml/min (GHSV 898 $h^{-1}$). These results show the potential to scale-up this plasma-catalytic process for $CO_2$ methanation.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims and drawings), and/or all of the steps of any method or process so disclosed, may be combined in any combination, except combinations where at most some of such features and/or steps are mutually exclusive.

Each feature disclosed in this specification (including any accompanying claims, and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims and drawings), or to any novel one, or any novel combination, of the steps of any method or process so disclosed.

The invention claimed is:

1. An apparatus for forming methane from carbon dioxide and hydrogen, the apparatus comprising:

a dielectric barrier discharge, DBD, device arranged to generate a plasma; and a passageway having an inlet for the carbon dioxide and the hydrogen and an outlet for the methane and including therein a catalyst comprising nickel on a surface of a support comprising alumina, wherein the catalyst comprises nickel particles having a mean particle diameter in a range from 1 nm to 10 nm and wherein the catalyst comprises manganese in a range from 0.01 to 10 wt. % by weight of the alumina support, wherein the passageway extends, at least in part, through the DBD device wherein, in use, the carbon dioxide is exposed to the catalyst in the presence of the hydrogen in the generated plasma, thereby forming the methane from at least some of the carbon dioxide and the hydrogen.

2. The apparatus according to claim 1, wherein the catalyst comprises nickel in a range from 1 to 35 wt. % by weight of the alumina support.

3. The apparatus according to claim 1, wherein the catalyst comprises metallic nickel.

4. The apparatus according to claim 1, wherein the catalyst comprises one or more rare earth elements, one or more first row and/or second row transition metals or one or more alkaline metals or mixtures thereof.

* * * * *